United States Patent
Yachia et al.

(10) Patent No.: US 6,398,718 B1
(45) Date of Patent: Jun. 4, 2002

(54) INTRAVESICULAR DEVICE

(75) Inventors: Daniel Yachia, Herzliya on Sea; Eran Hirszowicz, Ramat-Chen, both of (IL)

(73) Assignee: Innoventions, Inc., Edina., MN (US)

(*) Notice: Subject to any disclaimer, the term of this patent is extended or adjusted under 35 U.S.C. 154(b) by 0 days.

(21) Appl. No.: 09/594,641

(22) Filed: Jun. 15, 2000

(51) Int. Cl.⁷ .................... A61F 2/00; A61M 37/00
(52) U.S. Cl. ........................ 600/29; 604/93.01
(58) Field of Search ............... 600/29, 30; 604/103.9, 604/323, 264; 606/41; 607/88; 128/899

(56) References Cited

U.S. PATENT DOCUMENTS

| | | | |
|---|---|---|---|
| 4,055,178 A | 10/1977 | Harrigan | 128/260 |
| 4,258,705 A | 3/1981 | Sorenson et al. | 128/1 R |
| 4,804,375 A * | 2/1989 | Robertson | 604/323 |
| 4,834,704 A | 5/1989 | Reinicke | 604/51 |
| 4,850,963 A | 7/1989 | Sparks et al. | 600/29 |
| 4,871,542 A | 10/1989 | Vihardt | 424/423 |
| 5,019,032 A | 5/1991 | Robertson | 600/29 |
| 5,030,199 A | 7/1991 | Barwick et al. | 600/29 |
| 5,188,109 A | 2/1993 | Saito | 128/635 |
| 5,234,409 A | 8/1993 | Goldberg et al. | 604/96 |
| 5,334,197 A | 8/1994 | Kriesel et al. | 604/132 |
| 5,443,470 A | 8/1995 | Stern et al. | 607/98 |
| 5,472,441 A * | 12/1995 | Edwards et al. | 606/41 |
| 5,513,659 A | 5/1996 | Buuck et al. | 128/885 |
| 5,579,781 A | 12/1996 | Cooke | 128/733 |
| 5,604,531 A | 2/1997 | Iddan et al. | 348/76 |
| 5,653,689 A * | 8/1997 | Buelna et al. | 604/103.9 |
| 5,704,353 A | 1/1998 | Kalb et al. | 128/634 |
| 5,732,714 A | 3/1998 | Morrissey et al. | 128/846 |
| 5,762,599 A * | 6/1998 | Sohn | 600/30 |
| 5,800,478 A * | 9/1998 | Chen et al. | 607/88 |
| 5,806,527 A | 9/1998 | Borodulin et al. | 128/885 |
| 5,989,230 A * | 11/1999 | Frassica | 604/264 |
| 6,039,967 A | 4/2000 | Ottoboni et al. | 424/426 |
| 6,066,088 A * | 5/2000 | Davis | 600/29 |

\* cited by examiner

*Primary Examiner*—Eric F. Winakur
*Assistant Examiner*—Nikita R Veniaminov
(74) *Attorney, Agent, or Firm*—Ladas & Parry

(57) ABSTRACT

A resiliently flexible body having a non-spherical shape and having a magnetizable portion for use in sealing an anatomical cavity such as a urinary bladder. The body is compressed and then inserted into the cavity. In the cavity the body is experimented and positioned at the cavity outlet. The body is rotated in the outlet using a hand-held magnet between a sealing orientation in which the outlet is sealed, and a non-sealing orientation in which fluid, such as urine, can flow out of the cavity.

52 Claims, 22 Drawing Sheets

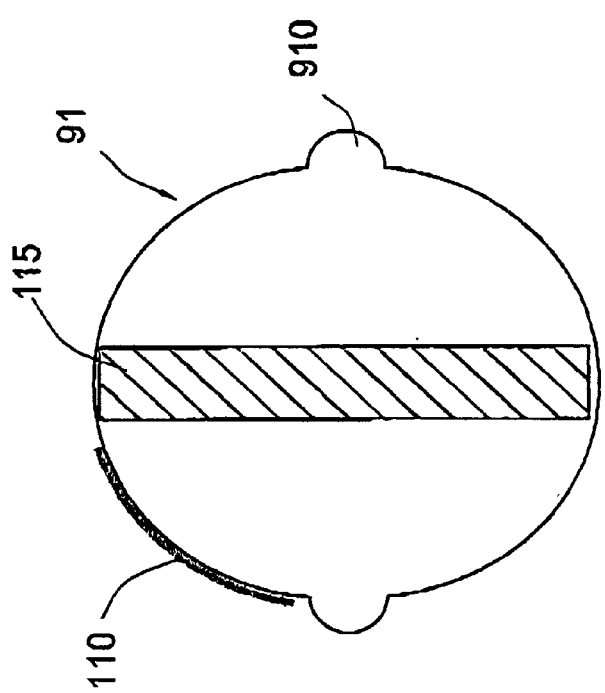
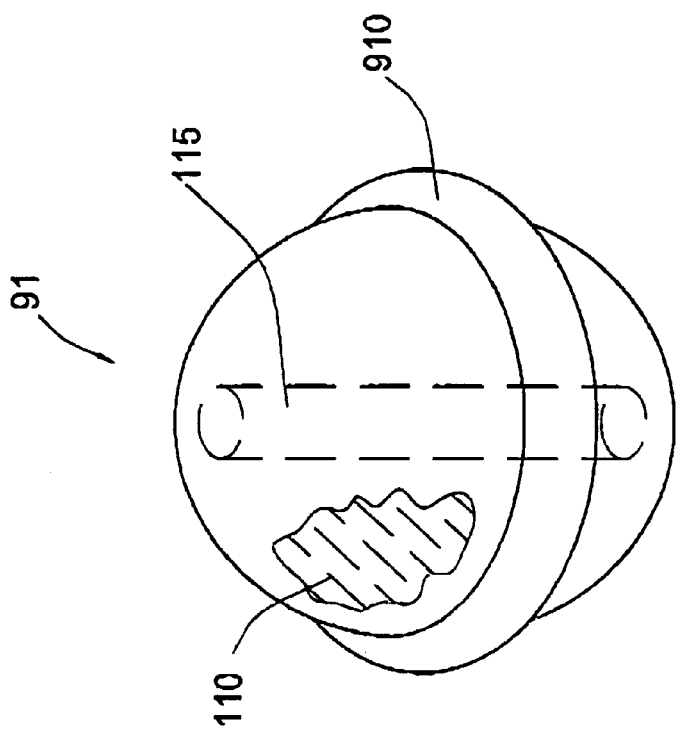
FIG. 9B
FIG. 9A

US 6,398,718 B1

INTRAVESICULAR DEVICE

FIELD OF THE INVENTION

The invention is in the field of medical devices. More specifically, the invention relates to devices for the treatment of urinary incontinence.

BACKGROUND OF THE INVENTION

Several disorders of the urinary tract are known. Among these are urinary incontinence, chronic urinary tract infections, urinary bladder tumors.

Urinary Incontinence

Urinary incontinence mostly affects women (approximately 10 million in the U.S.A. alone) primarily after childbirth or due to old age. In men, urinary incontinence often occurs as a complication of surgery or old age (approximately 3 million in the U.S.A).

Incontinence has serious economic, health, social and psychological consequences. Its estimated cost to the health system in the United States in 1993 was US $16 billion. It leads to chronic and severe skin irritation in the genital area, an increase in urinary infections and urosepsis. Fear of incontinence and odors in public cause incontinent people to severely restrict their social activities. The impact on the mental health of the affected people may be even more devastating than the social and health consequences. They suffer severe embarrassment, loss of self-esteem, depression and anxiety.

Urinary incontinence can be divided into four groups:

Stress Incontinence—is the involuntary release of urine due to a sudden increase in the intra-abdominal pressure caused by laughing,, sneezing, coughing, running, etc. This is the most common type of incontinence and in women may be the result of anatomical changes in the pelvic organs after childbirth, estrogen deficiency, unsuccessful surgical repairs for incontinence or pelvic irradiation. In men, it often happens after surgery for benign enlargement of the prostate gland or after radical removal of the prostate.

Total Incontinence—is the continuous leak of urine entering the bladder due 15 to failure of the sphincteric muscles.

Urge Incontinence—is involuntary loss of urine due to involuntary bladder contractions. This type of incontinence mostly affects the elderly who leak until they reach a toilet.

Mixed Incontinence—is a combination of stress and urge incontinence. This condition is more common in elderly women than men.

Ideally, treatment of incontinence should provide permanent dryness and is easy to perform.

Phannacological treatments of bladder dysfunctions are based either on estrogen replacement for treating postmenopausal vaginal and urethral atrophy or on agents affecting the tonus of the bladder muscle. Since affected elderly women suffer from both hormonal deficiency and urinary incontinence, both types of agents are usually prescribed simultaneously.

Surgical treatments are based on restoring the anatomical changes causing the incontinence. Although in the short-term most surgical procedures restore continence, the long-term prognosis is usually unsatisfactory. Moreover, surgery entails morbidity and high expenses.

Conservative/behavioral treatments are based on pelvic floor muscle exercises, bladder training, biofeedback, vaginal cones, low-frequency electrostimulation of pelvic floor muscles, intravaginal bladder neck support pessaries, urethral meatus suction cups and intraurethral devices. Conservative treatments are time consuming and require the patients' understanding, cooperation and persistence.

Devices which have been used to obtain almost immediate dryness in incontinent people can be divided into two groups:

(1) Urethral Plugs/Inserts

These comprise a flexible rod having, a 14 Ch. (approximately 4.5 mm) diameter and a length adjusted to fit the length of the patient's urethra. The rod has an inflatable device on its bladder end and a flange at other end. After insertion of the device, the device is inflated in the bladder. The device and the flange, maintain the device in its proper position within the urethra. The device and rod form a mechanical barrier to retain the urine within the bladder. The device must be deflated and the device removed and discarded prior to voiding,. Such inserts are known in the art, for example, the device known as RELIANCE produced by UroMed Corp., U.S.A. Since insets are discarded after each voiding and replaced with a new one by the patient, manual dexterity of the patient is required. Insertion of an insert into a female has the risk of pushing vaginal and perineal bacteria into the bladder and insertion of an insert a few times a day increases this risk The inconvenience of removing and inserting a new device and its costs, in addition to the infection risk, are the major disadvantages of these devices.

(2) Valve Catheters

These comprise a tube with a valve at one end. The bladder end of the device typically has a device or flanges for retaining the device in place and a flange at the other end to prevent migration into the bladder. The valve is opened for voiding through the lumen of the catheter with the help of an external magnet. The tube typically has a 18 Ch. (6 mm.) to 20 Cb. (approximately 7 mm) diameter and a length adjusted to fit the patient's urethra. For male incontinence, an active intraurethral Foley-type catheter is used. This device has a retaining, device at its bladder end and another smaller device under the prostate for fixing the device in place. The magnet activated valve is situated at the end of the device near the distal end of the urethra. Active inserts are typically left indwelling up to 4 weeks and are then replaced.

Examples of such catheters are disclosed in U.S. Pat. Nos. 5,030,199 and 5,234,409. Valve catheters are more convenient for the patient than the inserts; however, in females they cause ascending infection because they connect the bladder with the vulva which is rich in pathogenic bacteria, especially *Escherichia Coli*. Even with continuous use of antibiotics, infection is inevitable in the majority of cases. During prolonged use of cathetersor inserts in female patients, a relaxation of the urethra occurs and the patients may start to leak around the device. Unfortunately valve catheters and inserts are unavailable in increasing diameters.

A significant disadvantage of both the inserts and the valve catheters is the discomfort felt by the patient especially when sitting and during sexual intercourse (felt by the patient and the partner).

The present invention therefore provides a device for the treatment of urinary incontinence in which the disadvantages of the prior art devices are substantially reduced or eliminated.

(3) Urinary Bladder PIugs

U.S. Pat. No. 4,850,963 to Sparks et al. discloses a bolus for insertion in to a urinary bladder for the treatment of urinary incontinence. The bolus contains a ferromagnetic material and has a specific gravity greater than that of urine. The bolus is maintained at the urinary bladder outlet to the urethra under the influence of gravity so as to prevent the flow of urine into the urethra. For voiding, the bolus is displaced from the opening using an external magnet.

Urinary Tract Infections

Nearly half of all women experience urinary tract infection (UTI) at some point in their lifetime and most of these infections are confined to the bladder. Isolated UTIs can be treated by short and effective antibiotic treatment. However, recurrent UTIs often occur in women due to antibiotic resistant bacteria. In this case complicated infections often exhibit multidrug resistance and necessitate longer antimicrobial drug administrations.

Treatment of UTIs often requires urinary levels of antimicrobial drugs that are several hundred times greater than those allowable in the blood. Many antibacterials cannot be used in UTI because, when taken orally or intravenously, they do not attain the required concentration in the urine, without exceeding the allowable limit in the blood. It would therefore be desirable to be able to continuously introduce antimicrobial drugs continuously and directly into the bladder.

Bladder Tumors

Even after resection, bladder tumors may not only recur but may also invade deeper in the bladder wall. Due to the heterogenity of these tumors (from low-grade tumors showing a benign course to highly malignant high-grade tumors), there does not exist a single approach to the surveillance and treatment of these tumors. Intravesical drug therapies are often used for reducing tumor recurrence. In this approach an immunotherapeutic or chemotherapeutic agent is inserted into the bladder through a catheter. This treatment is typically repeated once a week for 6 weeks and then once a month for a period of 6–12 months. However, periodic treatment has not been established as being effective in altering the progression of the tumor. Continuous local treatment with chemotherapeutic or radioactive materials may treat or prevent not only superficial tumors but also deep tumors as well. It would therefore be desirable to be able to introduce antitumoral drugs continuously and directly into the bladder.

Bladder Dysfunction

During filling, the bladder muscle relaxes for keeping the intravesical pressure low while it contracts for voiding. Certain diseases such as spinal cord injuries, diabetes, multiple sclerosis, or hormonal changes after menopause or old age in both sexes may cause a hypo contractility or, paradoxically, hyper contractility of the muscle. In atonic bladder, pharmacological treatment is not very effective. In hyperreflexic bladder, drugs for relaxing the bladder cause constipation and mouth dryness and are therefore not tolerated well by the patients.

Diagnosis of bladder dysfunction requires continuously monitoring various bladder parameters during filling and/or voiding. These measurements usually are made by inserting a catheter connected to a measuring device into the bladder. This is done for example, in uroflowmetry (measurement of urinary flow rate) which is non-invasive, simple and inexpensive. However, its sensitivity and specificity are low. Cystometry is an invasive technique for measuring bladder capacity, compliance and muscle tonus. Pressure-flow study is an invasive and costly test for distinguishing patients with low urinary flow due to obstruction or bladder antonia, from those with high intravesical pressure and high urinary flow. It is therefore a need in the art for a simple and inexpensive technique for intravesicular monitoring.

In the diagnostic procedure known as "urodynamics", the bladder is filled through a catheter, and the response of the bladder is monitored. Available 24 hour urodynamic monitors have catheters or wires passing trough the urethra, connecting sensors inserted into the bladder to a recorder. The connecting wires and catheters inadvertently introduce pathogenic bacteria from the genital areas into the bladder. It is therefore desirable to be able to monitor bladder function over several cycles of filling and voiding without the need for such wires or catheters.

Diagnosis of some intravesical pathological conditions often involves inserting an endoscope into the bladder and optically scanning the bladder walls. In cases of bleeding in the ureters or the kidneys, the observation of blood coming through the ureteral orifices allows determination of the origin of the bleeding. However, if the bleeding has temporarily stopped at the time of the examiation, or if the blood concentration in the urine is insufficient to make the urine red or pink, endoscopy is of little value in reaching a diagnosis. In such cases more invasive procedures are performed in order to enter the upper urinary tract. It is therefore desirable to be able to monitor the bladder over long periods of time.

Bladder shape during filling and its contraction during voiding is important for the diagnosis of certain bladder pathologies. These functions can be followed in fluoroscopy and by sonography. These techniques however are not accurate and cannot be used for monitoring changes in bladder shape over long periods of tie. It would therefore be desirable to be able to continuously image the bladder interior over long periods of time.

The present invention therefore provides a device for continuous monitoring of the bladder interior and for the treatment of bladder disorders in which the disadvantages of the prior art devices are substantially reduced or eliminated.

SUMMARY OF THE INVENTION

The present invention provides a flexibly resilient body having a non-spherical shape, for insertion into an anatomical cavity such as a urinary bladder. The non-spherical shape may be formed, for example, by introducing one or more grooves or protrusions onto the surface of a sphere or by introducing a channel through a sphere. The body may be completely solid, or may contain a fluid in an interior lumen. The body is compressed prior to insertion and then allowed to expand after insertion in the cavity. In the case of a body configured to contain a fluid in a lumen, the body may be inserted into the cavity in a collapsed state with no fluid in the lumen. After insertion the body is expanded by introducing the fluid into the lumen. The body has a magnetizable portion allowing it to be positioned in an outlet of the cavity by means of a hand-held magnet placed in the vicinity of the cavity. The hand-held magnet is also used to rotate the body in the outlet of the cavity.

The body is used for the intermittent sealing of the outlet for preventing inappropriate release of fluid from the cavity. Sealing the outlet involves rotating the body in the outlet into a sealing orientation in which fluid is unable to flow around or through the body. Rotation of the body is done without displacing it from the outlet. Unsealing the outlet to allow voiding of the cavity involves rotating the body into a non-sealing orientation in which fluid flows around or through the body. The body is preferably coated with a hydrophilic coating to reduce frictional forces between the body and the wall of the outlet in order to facilitate rotation of the body in the outlet.

The body may also be used for such purposes as, for example, delivery of drugs, imaging thecavity, and measuring intravesicular parameters such as pressure in the cavity or the composition of a body fluid in the cavity such as urine.

The invention is entirely confined to the cavity As will become apparent in the description below, the body is easily inserted and removed. It may be left in the cavity for prolonged periods of time with minimal risk of encrusting or causing infections and is displaced within the cavity at will using a hand held magnet. The invention is comfortable for the patient and does not interfere with the daily activities of the patient including sitting, jogging, riding, or sexual intercourse.

In its first aspect the invention thus provides a resiliently flexible body having a magnetizable portion for use in medical procedures within an outlet of a cavity of an individual, the body having a non-spherical shape and configured to rotate within the outlet between a sealing orientation and a non-sealing orientation.

In its second aspect the invention thus provides a system for use in medical procedures within a cavity of an individual comprising a body of the specified type and one or more devices from the list comprising:

(a) an applicator for inserting the body into the cavity or for removing the body from the cavity, the applicator fitted at an end thereof with a gripping device for releasably gripping the body; and (b) a rotating member comprising a magnetizable portion for rotating the body in an outlet of the cavity between the sealing orientation and the non-sealing orientation.

In its third aspect the invention thus provides a method for treating urinary incontinence in an individual comprising the steps of:

(a) compressing a body of the specified type;

(b) inserting the body into a urinary bladder outlet of the individual;

(c) expanding the body in the urinary bladder outlet;

(d) rotating the body within the urinary bladder outlet into a sealing position for sealing the urinary bladder outlet; and (e) rotating the body within the urinary bladder outlet into an unsealing position for voiding the urinary bladder.

In its fourth aspect the invention thus provides a method for releasing one or more substances into a cavity of an individual comprising the steps of:

(a) loading the one or more substances into a body of the specified type, comprising a compartment containing the one or more substances;

(b) compressing the body;

(c) inserting the body into the cavity; and (d) expanding the body in the cavity.

In its fifth aspect the invention thus provides a method for monitoring the interior of a cavity of an individual comprising the steps of:

(a) compressing a body of the specified type, comprising one or more devices for monitoring the cavity;

(b) inserting the body into the cavity;

(c) expanding the body in the cavity; and (d) transmitting signals from at least one of the monitoring devices to a receiver.

In its sixth aspect the invention thus provides a method for imaging the interior of a cavity of an individual comprising the steps of:

(a) compressing a flexibly resilient body of the specified type, comprising a device for imaging the cavity;

(b) inserting the body into the cavity;

(c) expanding the body in the cavity; and (d) transmitting signals from the imaging device to a receiver.

In its seventh aspect the invention thus provides a method for releasing one or more substances into a cavity of an individual comprising the steps of:

(a) providing a body of the specified type, comprising a pump fed by a reservoir;

(b) loading the reservoir with the one or more substances;

(c) inserting the body into the cavity; and (d) activating the pump so as to release the one or more substances into the cavity.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

While the present invention will be described with reference to the urinary bladder, it should be understood that the invention may be used with any anatomical cavity having an outlet through which a fluid leaves the cavity.

Figure 1B:
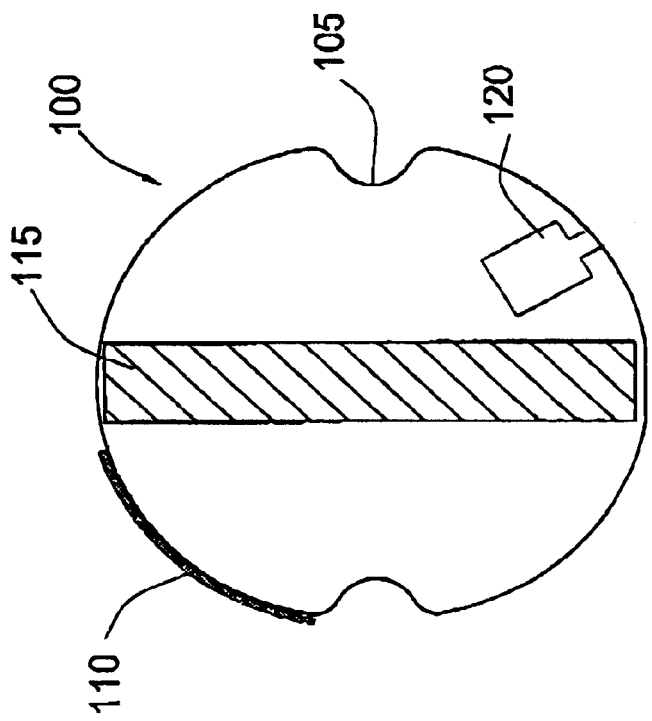
FIG. 1 shows a body in accordance with one embodiment of the invention.
Figure 1A:
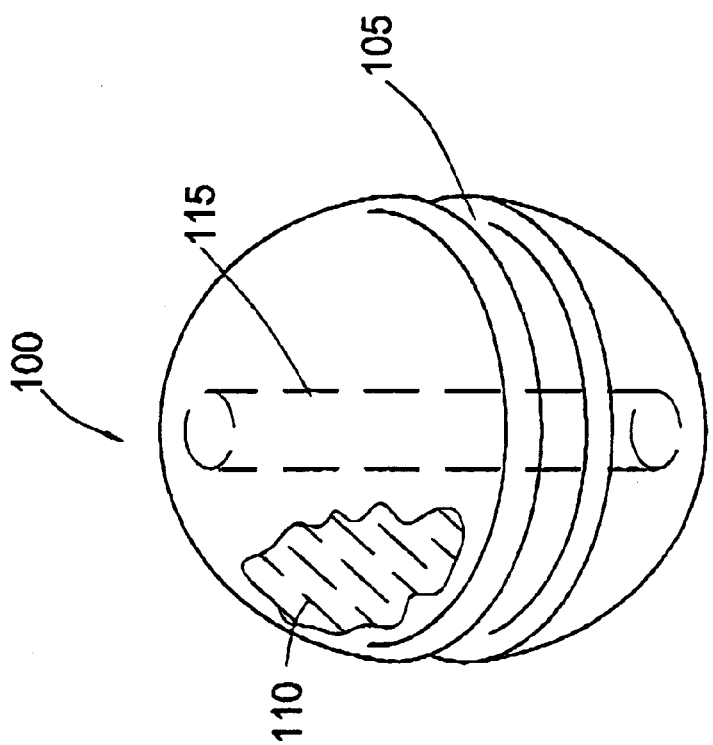

Reference is first made to FIG. 1 which shows an embodiment of the body in accordance with the invention. The body, generally designated as 100, is shown in a three-dimensional perspective in FIG. 1a, and in cross-section in FIG. 1b. The body in this embodiment is formed by introducing a circumferential groove 105 into a sphere. The body 100 may be made of a resiliently flexible elastic biocompatible material. Alternatively the body 100 may be a balloon formed from a flexible material and having an interior lumen configured to contain a fluid. The body may be coated on its outer surface with a hydrophilic coating 110. The body comprises a magnetizable portion. In the embodiment of the body 100 shown in FIG. 1, magnetizable portion consists of a metal rod 115 located in the interior of the body 100 and substantially perpendicular to the plane of the circumferential groove 105.

The body may have one or more chambers 120 for storing one or more substances. Such substances could be, for example, drugs, antibiotics or radioactive substances, etc. After insertion of the body 100 into the lumen of the urinary bladder, the substances are released from the body 100 into the bladder in order to achieve a desired effect.

Figure 2:
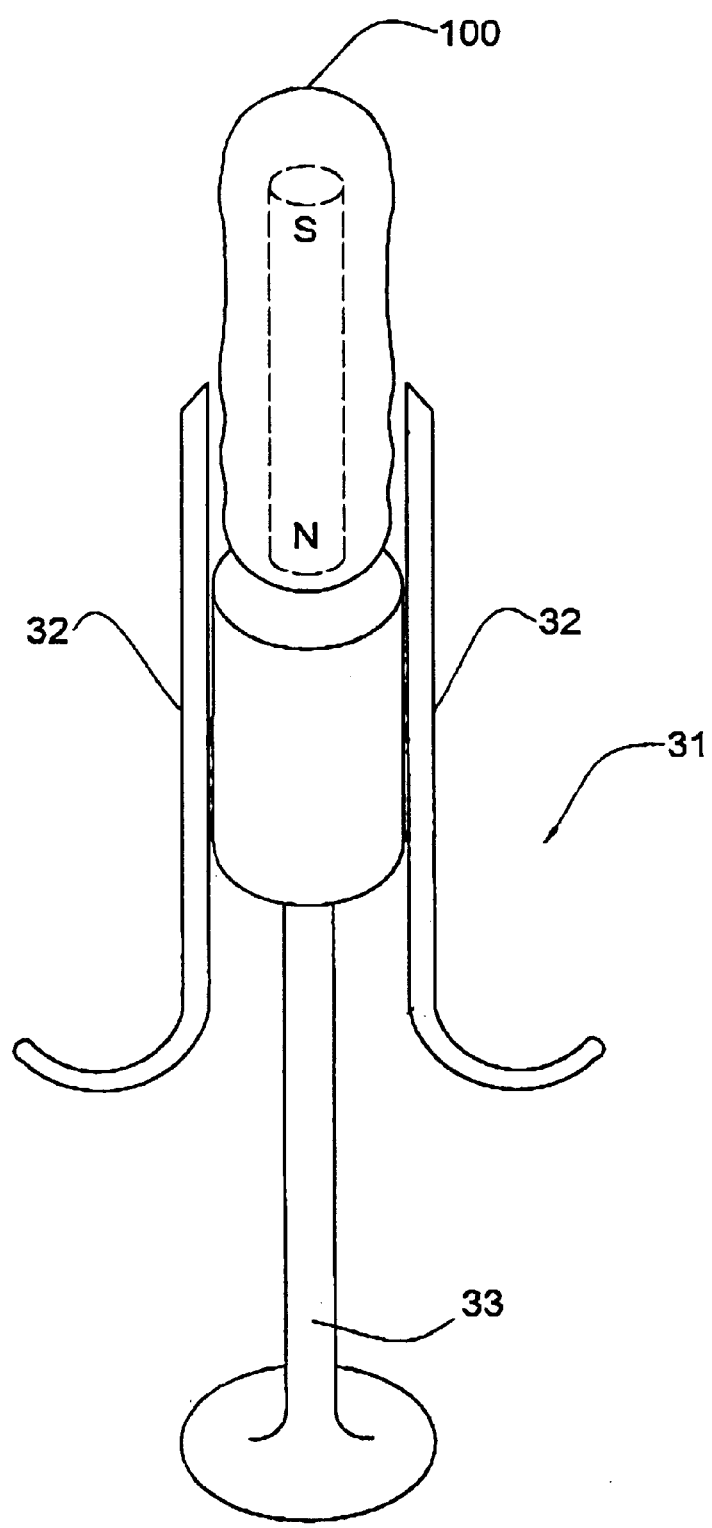
FIG. 2 shows an applicator for inserting a body according to the invention into the urinary bladder of an individual.
Figure 3:
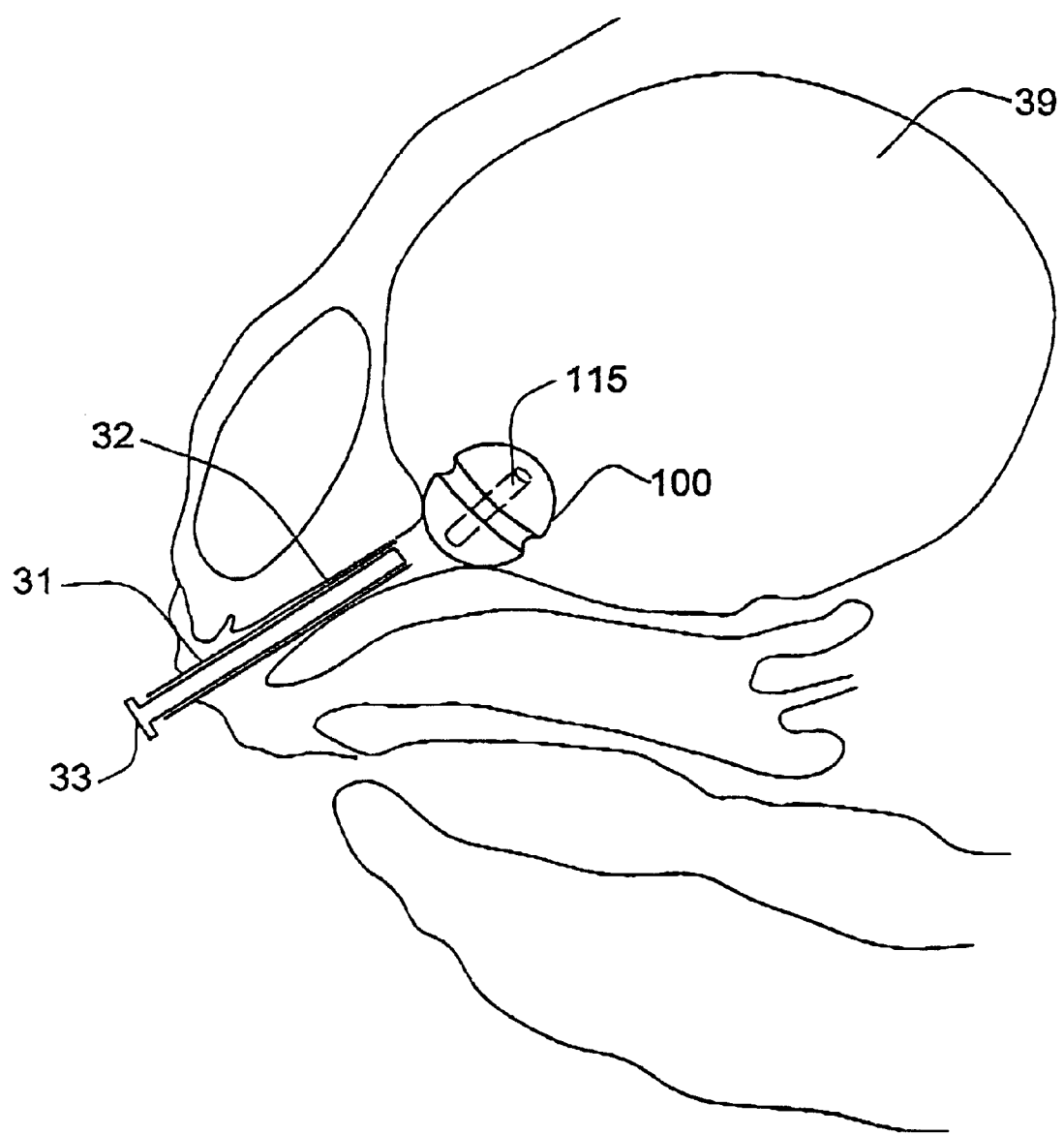
FIG. 3 shows a body after having been inserted into a urinary bladder with an applicator.

FIG. 2 shows an applicator 31 for inserting a solid body into the lumen of the urinary bladder of an individual. The applicator 31 consists of a slender cylindrical sheath 32 and a piston 33. When the body 100 is initially loaded into applicator it is maintained in a compressed state at the distal end 32 of the applicator. As shown in FIG. 3, the distal end 32 of the applicator-body combination is inserted into the urethra until it reaches the lumen of the bladder. The body 100 is then released from the applicator by pushing the body 100 from applicator 31 with pushing piston 33. The applicator is then removed from the bladder, leaving the body 100 in the bladder lumen 39. Following its release from the applicator into the bladder, the body regains its initial shape.

Figure 4:
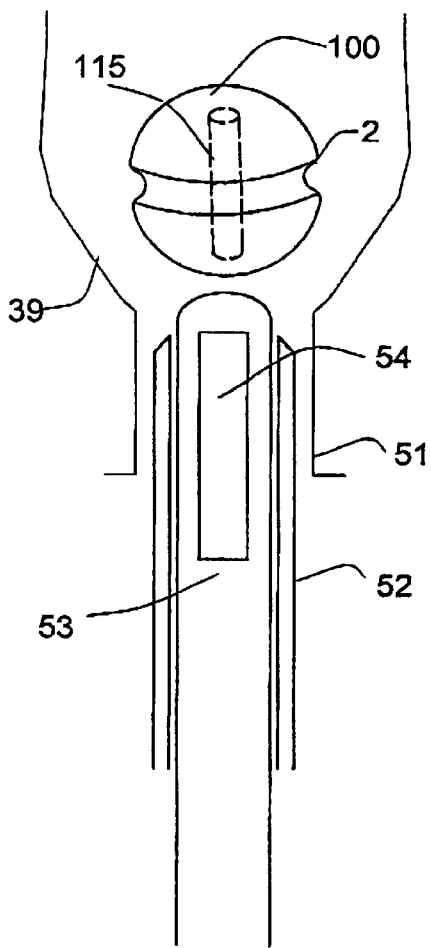
FIG. 4 shows a retrieval device for retrieving a body.
Figure 5:
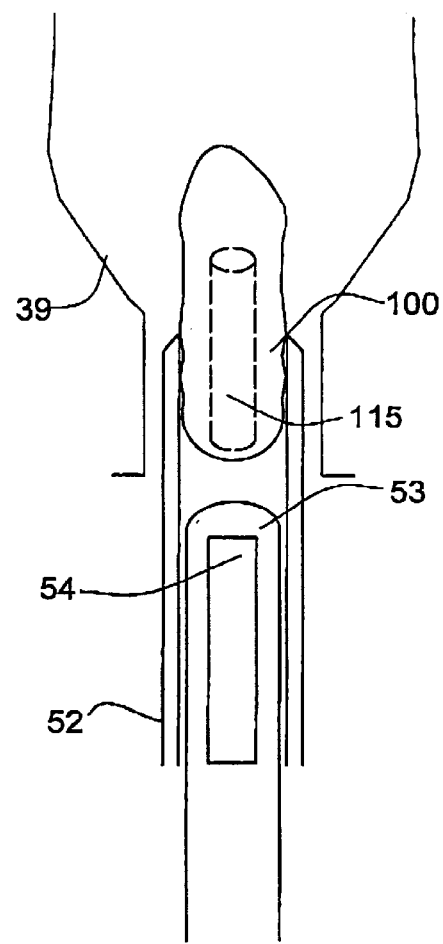
FIG. 5 shows the retrieval device shown in FIG. 4 holding a body.

FIG. 4 shows a retrieval device generally designated 51 for removing a solid body 100 from the bladder 39. A catheter 52 has a slender shaft 53 in its lumen which has at its distal end a magnetizable portion 54 so as to engage a body 100 at the distal tip by means of the magnetizable portion 115 associated with the body 100. As shown in FIG. 5, when probe 53 is then retracted, body 100 is deformed and brought into catheter 52. The retrieval device is then withdrawn from the patient together with the body 100.

Figure 13:
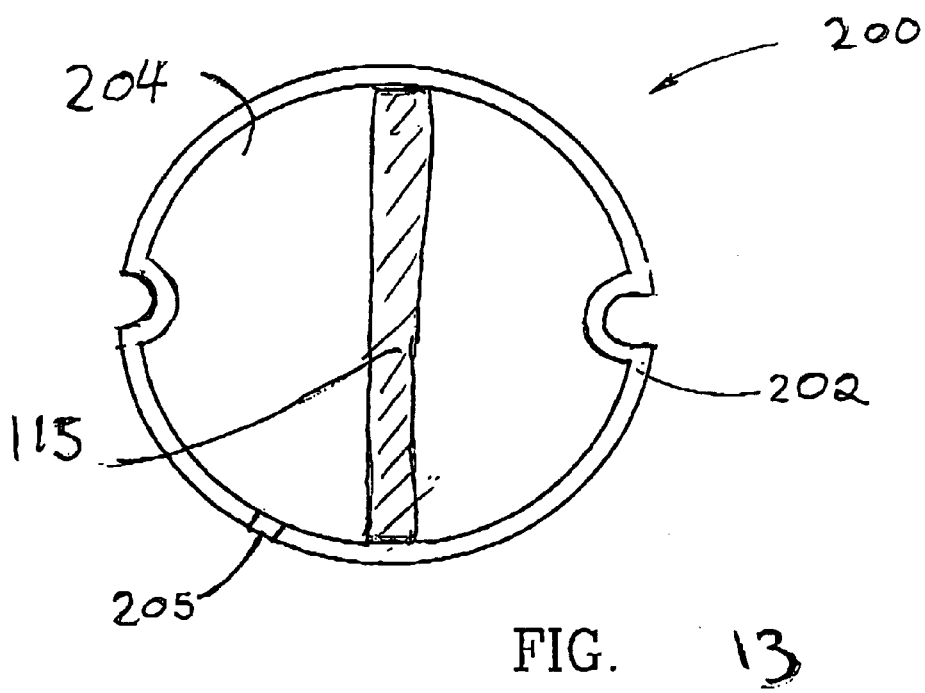
FIG. 13 shows various embodiments of the balloon according to the invention.

Reference is now made to FIG. 13 which shows a body in accordance with the invention generally designated as 200. The body 200 is a balloon having a wall 202 made of a flexible biocompatible material enclosing a lumen 204. Balloon 200 comprises a magnetizable portion 115 in the form of a metal rod extending along a diameter of the balloon 200. The lumen 204 of balloon 200 is configured to be filled with a biocompatible fluid, which may be presterilized such as air, water, saline or an oil such as liquid paraffin.

Figure 14:
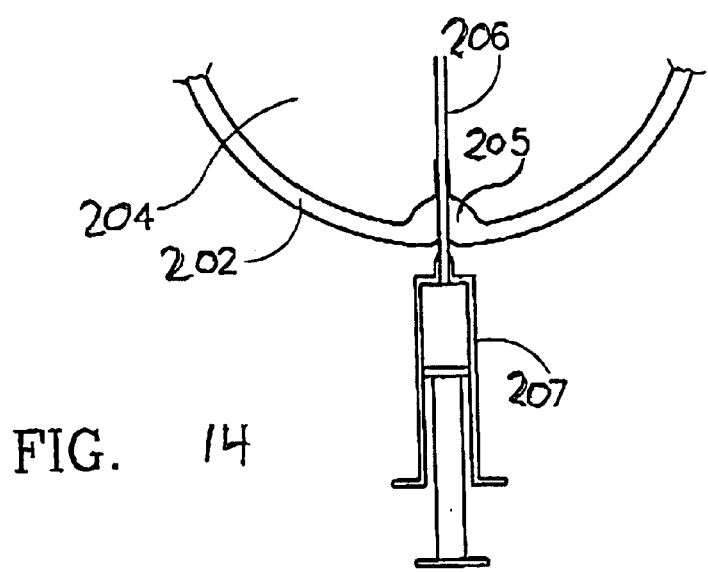
FIG. 14 shows a portion of a balloon according to the invention having a duck-bill valve.
Figure 15A:
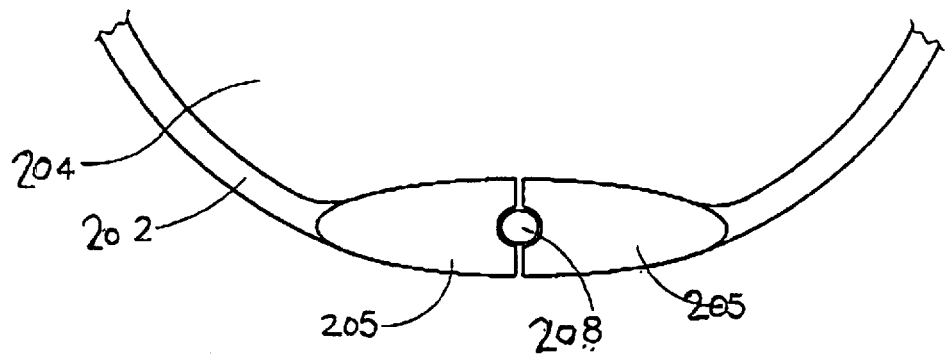
FIG. 15 shows a portion of a balloon according to the invention having a ball valve.
Figure 15B:
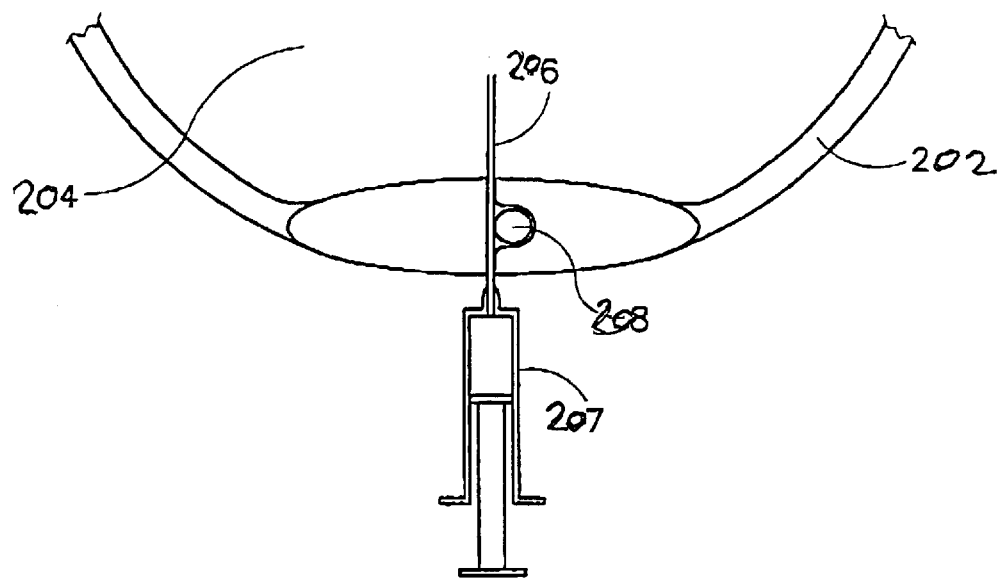
Figures 16A, 16B:
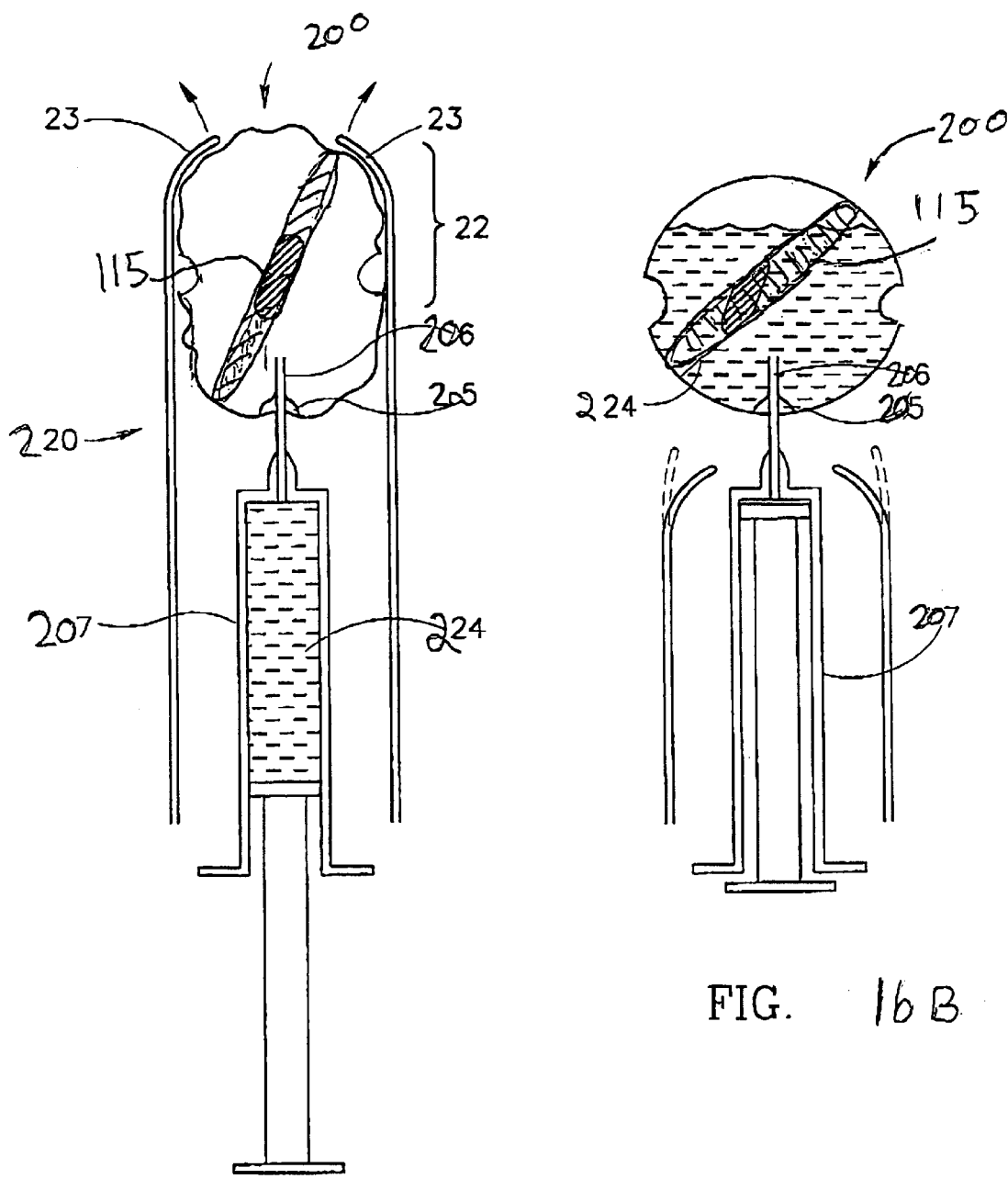
FIG. 16 shows a balloon fitted after having been inserted into the bladder.
Figures 17A, 17B:
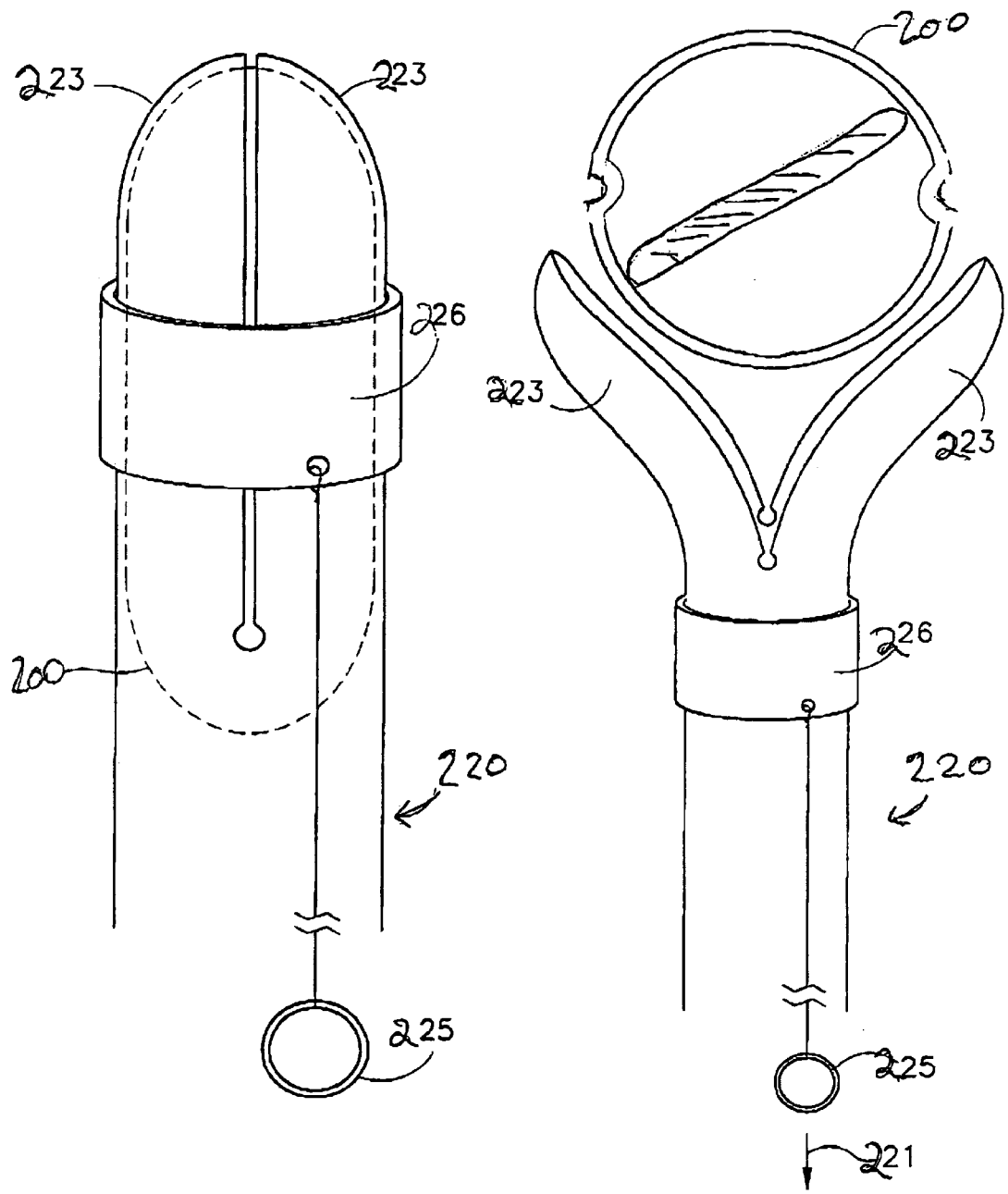
FIG. 17 shows a balloon filled before being inserted into the urinary bladder.

A self-sealing valve 205 in the wall of the balloon is used to fill the balloon. The valve 205 may be for example a duck-bill type valve as shown in FIG. 14 or a ball valve as shown in FIG. 15 in which a ball 208 may be in a sealing position (FIG. 15a) or an unsealing position (FIG. 15b). The canula 206 of a syringe 207 is inserted through the valve 205 into the lumen 204 of the balloon. The fluid injected into the lumen 204 causes the balloon to expand. After filling, the syringe needle 206 is withdrawn, and the valve 205 seals itself As shown in FIG. 16, the balloon may first be inserted into the bladder by means of an applicator 220 to be described below in detail (FIG. 16a) and following its release from the applicator into the bladder, the balloon is then filled with fluid 224 from a syringe 207 (FIG. 16b). Alternatively, as shown in FIG. 17a, the balloon 200 may be filled and compressed before being inserted into the bladder by means of applicator 220. The prefilled balloon is clutched by the flanges 223 which are initially kept closed by constraining sleeve 226 (FIG. 17a). After insertion of the applicator 220 with the prefilled balloon 200 into the urinary bladder, ring 225 is pulled as indicated by arrow 221 in FIG. 17b to urge the constraining sleeve 226 away from the flanges 223, allowing flanges 223 to open and release the prefilled balloon 200 into the bladder.

Figure 18:
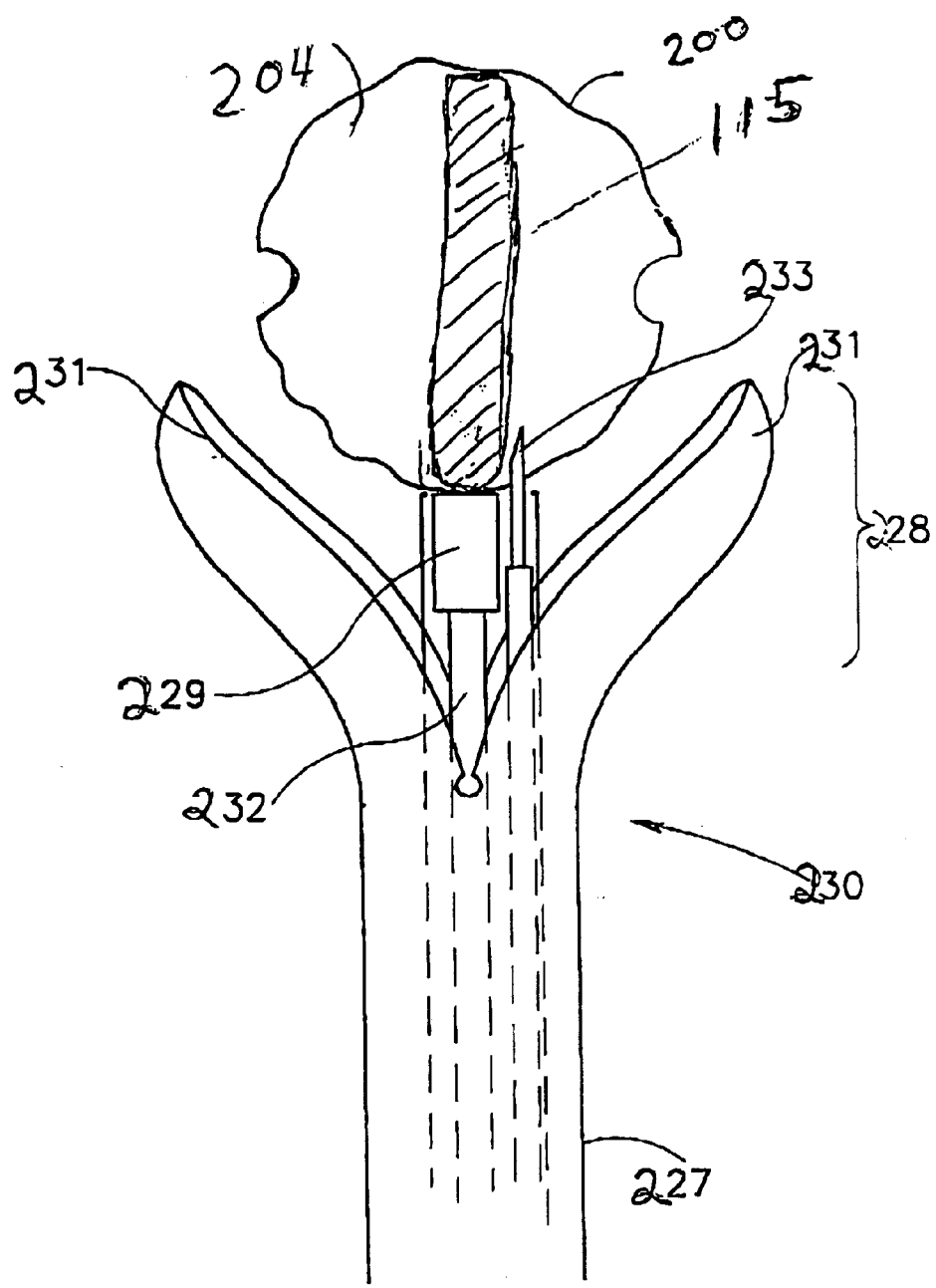
FIG. 18 shows a retrieval device for removing a balloon from the urinary bladder.

FIG. 18 shows a retrieval device generally designated as 230 for removing the balloon 200 from the bladder. A catheter 227 has at its distal end 228 a magnetizable portion 229 so as to hold the balloon 200 at the distal tip 228 by means of the magnetizable portion 115 associated with the balloon 200

The retrieval device 230 is inserted into a fall bladder. After opening the flanges 231 of the retrieval device, the engaging probe 232 with magnetizable portion 229 in its tip is inserted into the lumen of the full bladder so as to engage the magnetizable portion 115 of the balloon 200 and push the balloon into the lumen of the bladder. The probe 232 is then pulled so as to bring the balloon 200 into the grip of flanges 231 of the retrieval device. A piercer 233 is inserted into the balloon to drain the fluid contained in its lumen 204 into an attached syringe (not shown) or into the bladder lumen. The retrieval device 220 is then withdrawn from the bladder together with the deflated balloon 200.

Figure 6:
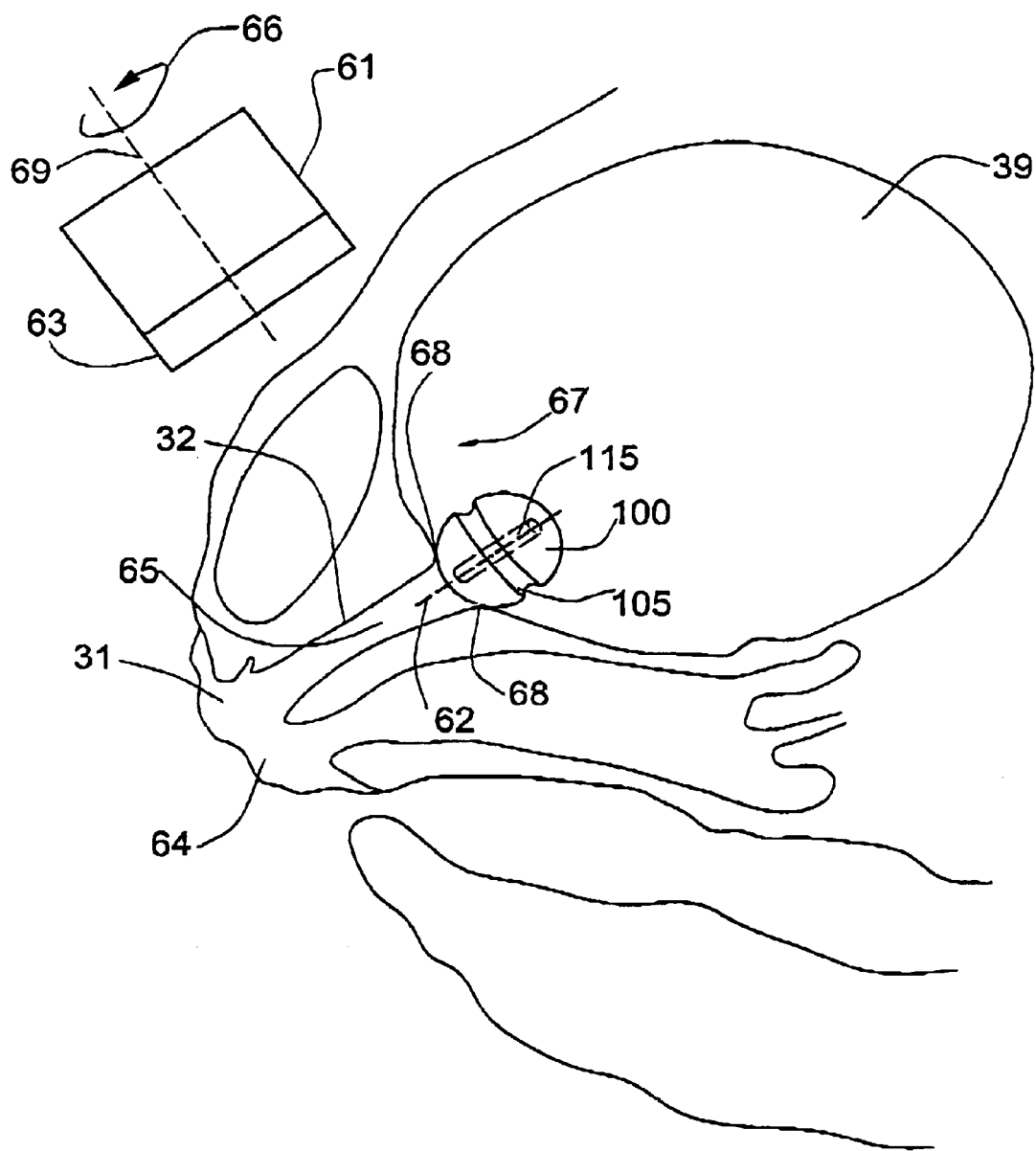
FIG. 6 shows use of a rotating member to rotate the body into a sealing orientation within the urinary bladder.
Figure 7:
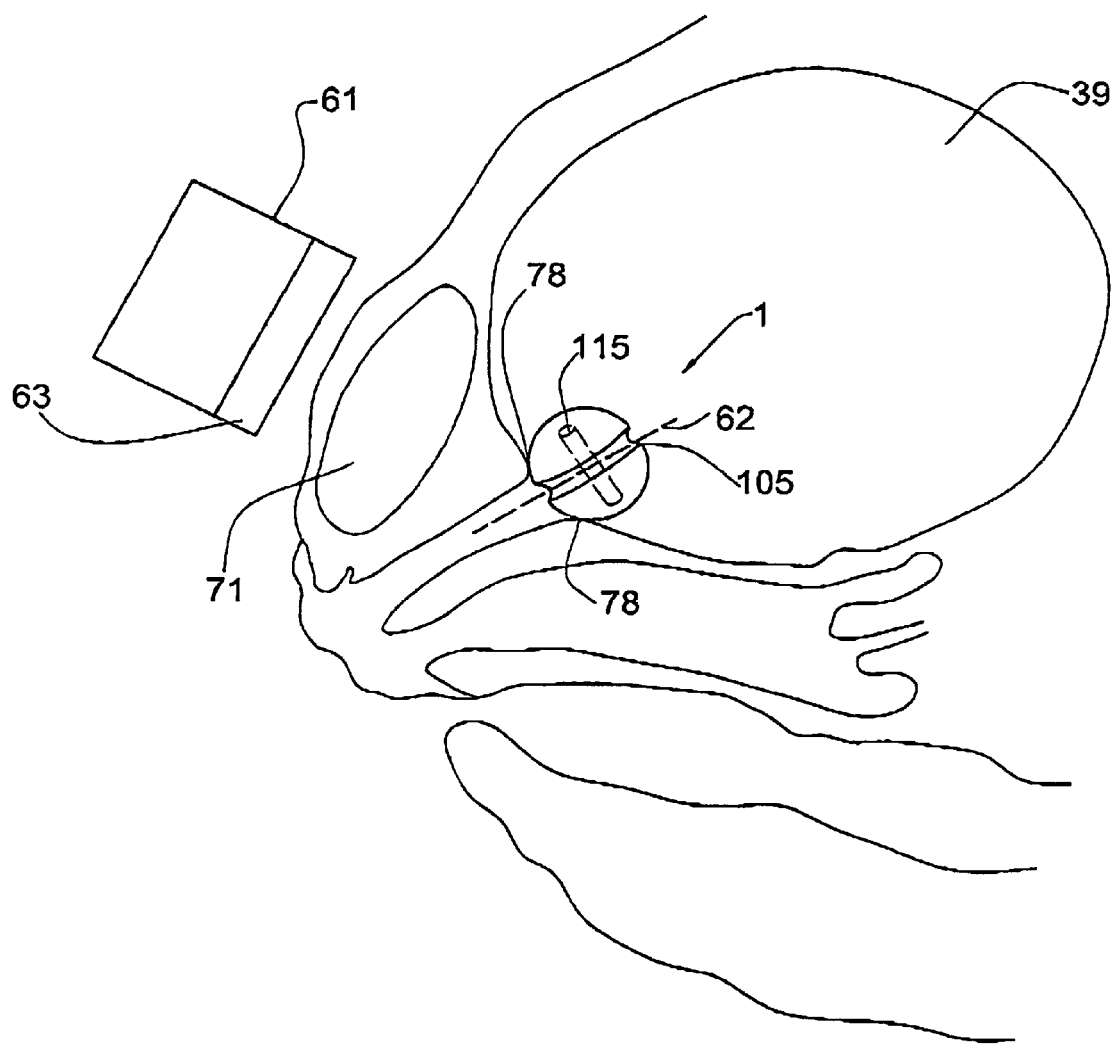
FIG. 7 shows use of a rotating member to rotate the body from a sealing orientation to a non-sealing orientation in the urinary bladder.

FIGS. 6 and 7 show use of a rotating member 61 used to position a body 100 having a magnetizable portion 115 within the outlet 65 of a urinary bladder in a female individual. Rotating member 61 is located outside the individual's body and comprises a magnetizable portion 63. The rotating member is placed at a location on the surface, of the individual's body over the outlet 65 so as to position the body in the outlet 65. Rotating the rotating member 61 around an axis 69 generally perpendicular to the surface of the individual's body, as indicated by arrow 66 causes the body 100 to rotate in the urinary bladder outlet 65.

FIG. 6 shows use of a body 100 for sealing the urinary bladder outlet in a female subject. Rotating member 61 is placed over the urinary bladder 39 and is rotated. Due to the magnetizable portion 63 associated with rotating member 61 and the magnetizable portion 115 associated with body, the body is rotated into the sealing orientation within the bladder outlet 65. In this orientation, the circumferential groove 105 lies in a plane perpendicular to the axis of the bladder outlet 65 indicated by the broken line 62. The body 100 contacts the outlet wall, in an annular region 68 so that urine is unable to flow around the body 100. As the amount of urine in the bladder increases, a hydrostatic pressure is exerted on the body further lodging it in the outlet 65 and reinforcing the seal. The invention is used similarly for sealing the urinary bladder outlet in male subjects As seen in FIG. 7, in order to open the urinary bladder for voiding, rotating member 61 is placed over the urinary bladder 39 and is rotated. Due to the magnetizable portion 115 of the body, the body is rotated into the unsealing orientation. In this orientation, the circumferential groove 105 lies in a plane parallel to the bladder outlet axis 62. The body now contacts the outlet wall in a region 78 consisting of two separated circular arcs. This allows urine to flow through the circumferential groove 105 around the body 100 as indicated by arrow 73. After voiding, the body 100 is rotated in the bladder outlet back to the sealing orientation by the rotating member 61 so as to seal the outlet again as shown in FIG. 6.

Figure 8:
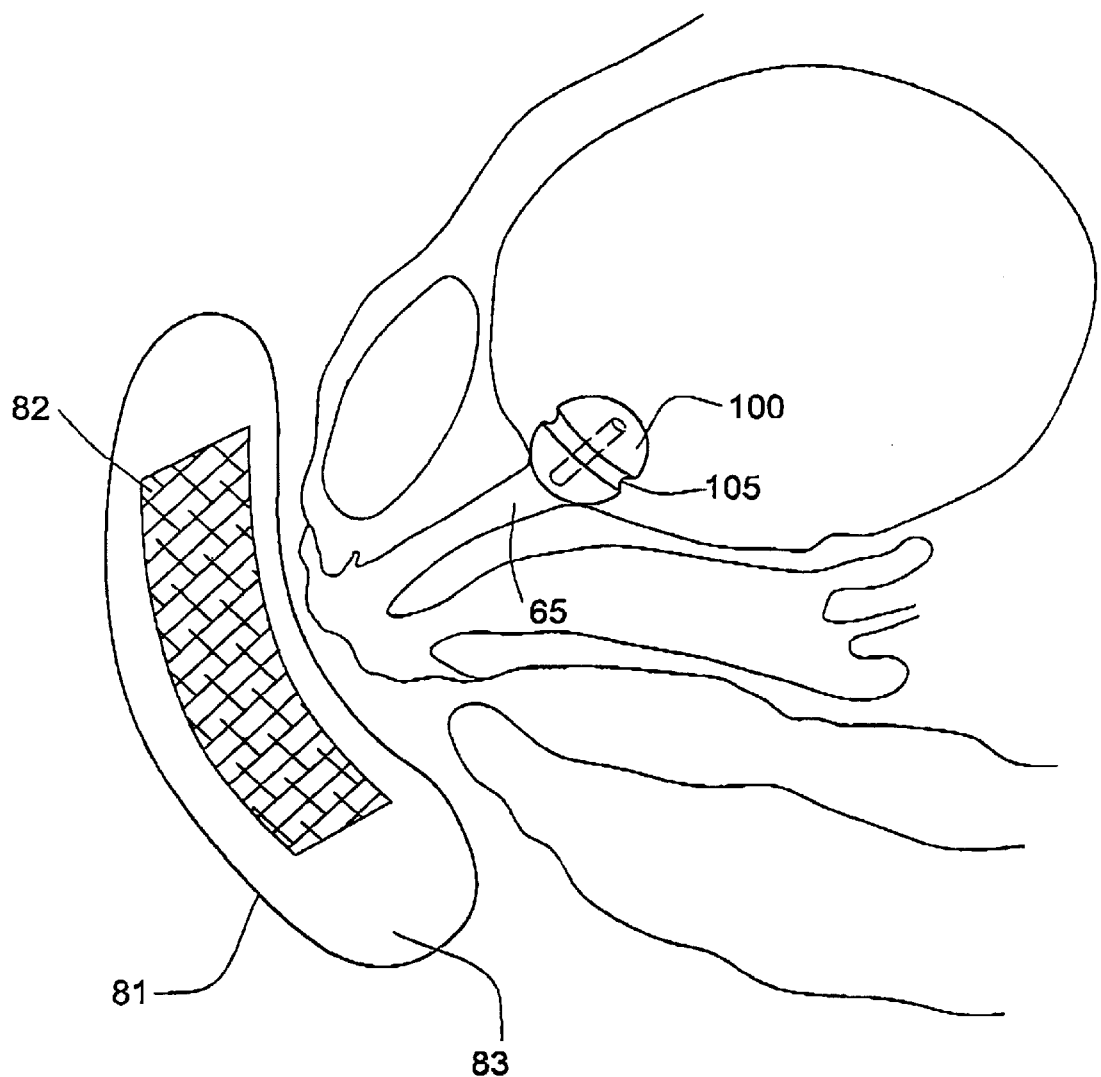
FIG. 8 shows use of an immobilizing member.

FIG. 8 shows use of an immobilizing member 81 comprising a magnetizable portion 82 affixed to the surface of the individual's body so as to maintain body 100 in the urinary bladder outlet 65. Magnetizable portion 82 of immobilizing member 81 may be enclosed in a coating 83 so as to form, for example, a hygienic pad. The immobilizing member may be affixed to the surface by means of tape, or by pressure applied to it by the individual's underwear.

Reference is now made to FIG. 9 which shows several other embodiments of the body in accordance with the invention These embodiments have components in common with the embodiment of FIG. 1 that have been indicated by the same numerals in both figures.

In the embodiment shown in three-dimensional perspective in FIG. 9a and in cross-section in FIG. 9b, the body generally indicated by 91 is formed by introducing a circumferential protrusion 910 onto a sphere. The body 91 is in a sealing orientation when the circumferential protrusion 910 lies in a plane perpendicular to the outlet axis 62, and is in the non-sealing orientation when the circumferential protrusion 910 lies in a plane parallel to the outlet axis 62.

Figure 9D:
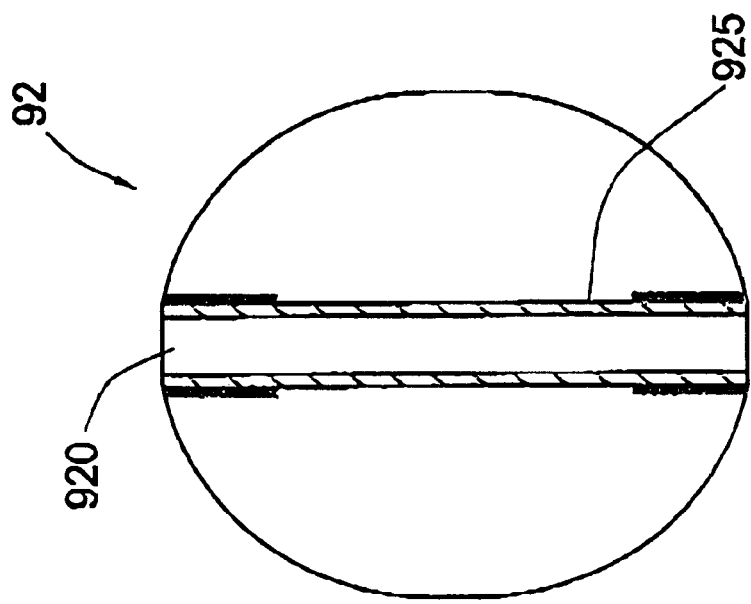
FIG. 9 shows other embodiments of the body in accordance with the invention.
Figure 9C:
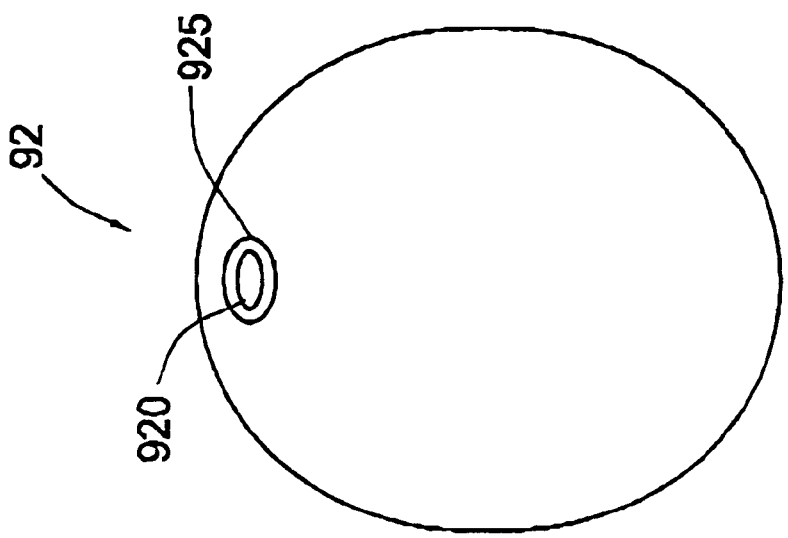

In the embodiment shown in three-dimensional perspective in FIG. 9c and in cross-section in FIG. 9d, the body generally indicated by 92 is formed by introducing into a sphere a channel 920 extending along the entire length of a diameter of the sphere. The channel 920 is lined with a hollow cylindrically-shaped magnet 925. The body 92 is in a sealing orientation when the channel 920 lies in a plane perpendicular to the outlet axis 62 and is in the non-sealing, orientation when the channel 920 lies in a plane parallel to the outlet axis 62.

Figure 9F:
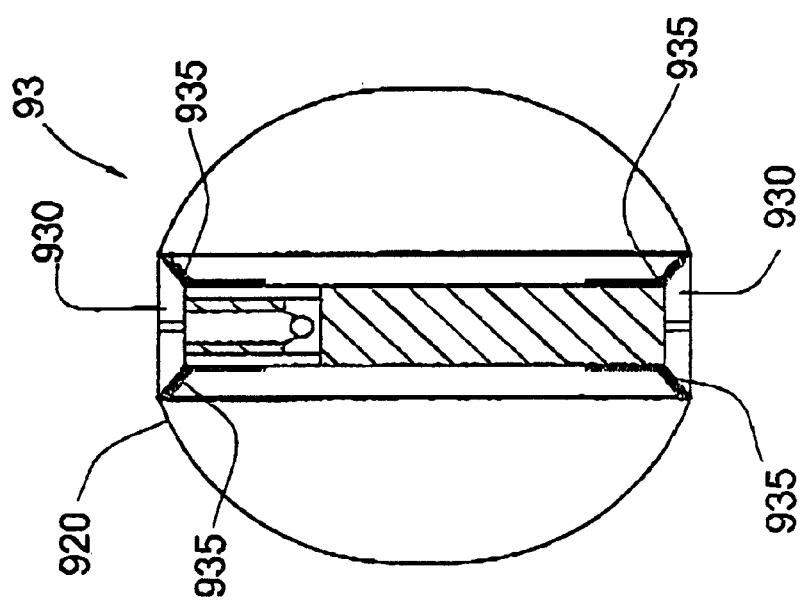
Figure 9E:
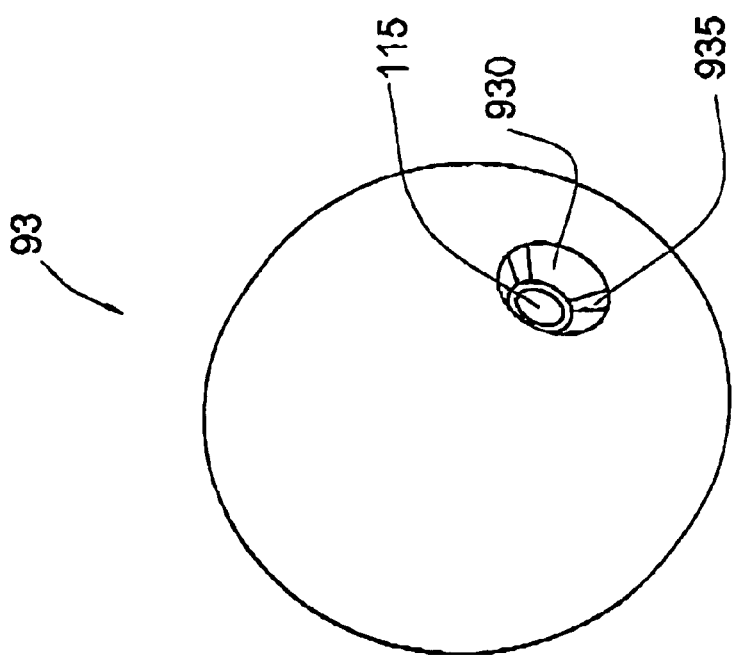

In the embodiment shown in FIG. 9e in three-dimensional perspective and in FIG. 9f in cross-section, the body 93 is formed by introducing into a sphere a channel 930 extending along the entire length of a diameter of the sphere. A rod-shaped magnetizable portion 115 is located in the interior of hole 930 and is supported by several arms 935 that project from the wall 940 of the body 93 to the magnetizable portion 115. The body 93 is in a sealing orientation when the hole 930 lies in a plane perpendicular to the outlet axis 62 and is in the non-sealing orientation when the hole 930 lies in a plane parallel to the outlet axis 62.

Figure 9H:
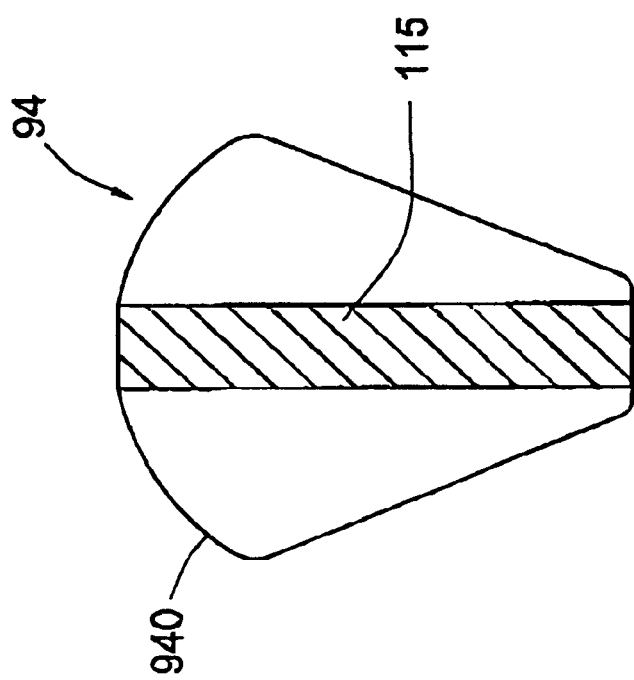
Figure 9G:
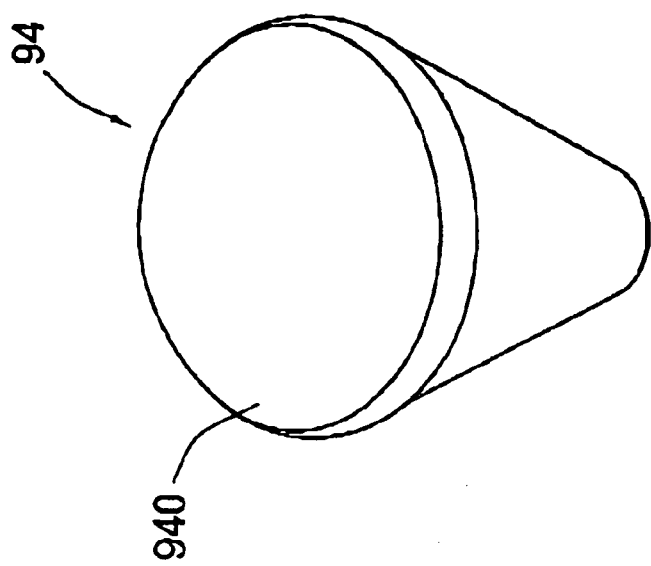

In the embodiment shown in FIG. 9g in three-dimensional perspective and in FIG. 9h in cross-section, the body 94 has a generally tapered shape. The wide end 940 of the body 94 is a hemispherical surface. The body 94 is in a sealing orientation when the wide end 940 of the body 94 is in contact with the bladder wall in proximity to the bladder outlet The body 94 is in a non-sealing orientation when the wide end 940 is distal to the bladder outlet.

Figure 9J:
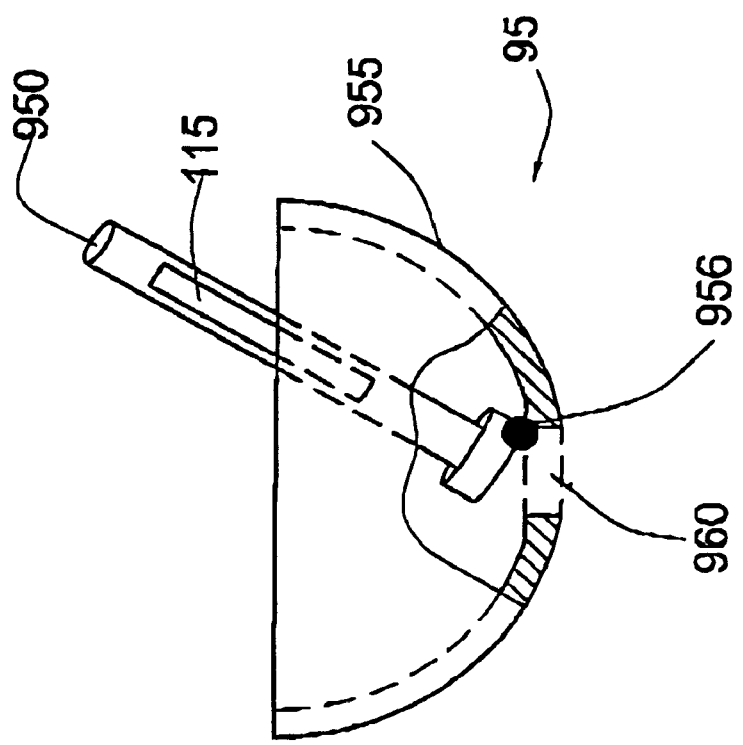
Figure 9I:
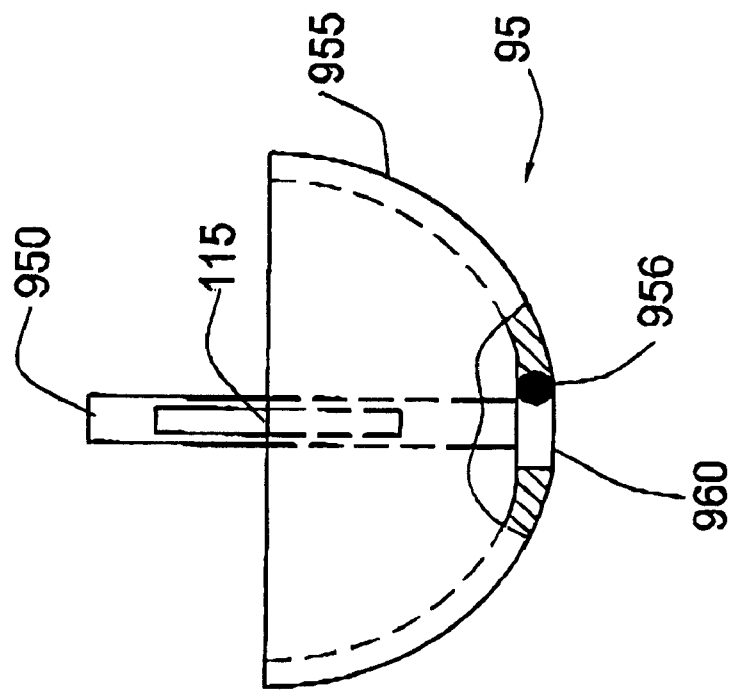
Figure 9K:
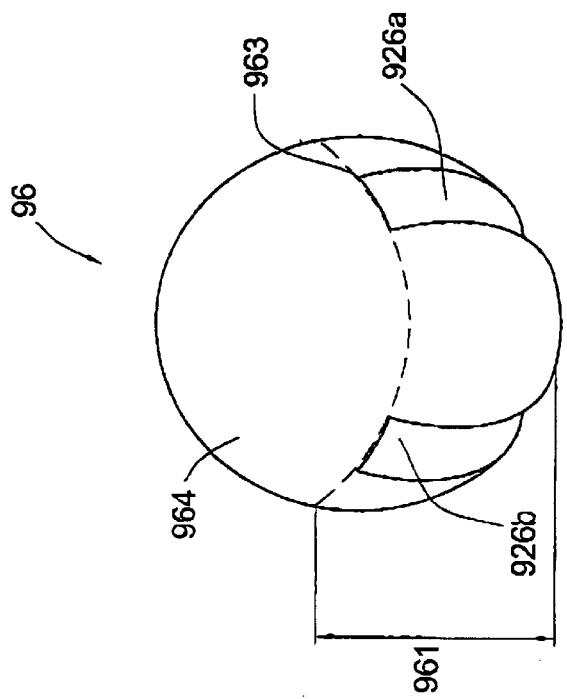
Figure 9L:
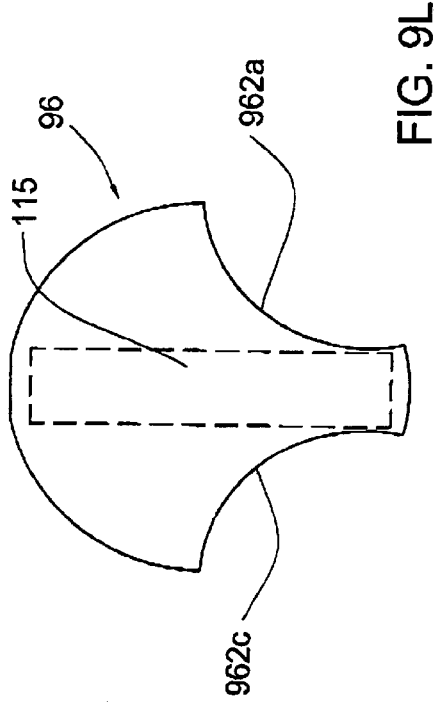
Figure 9M:
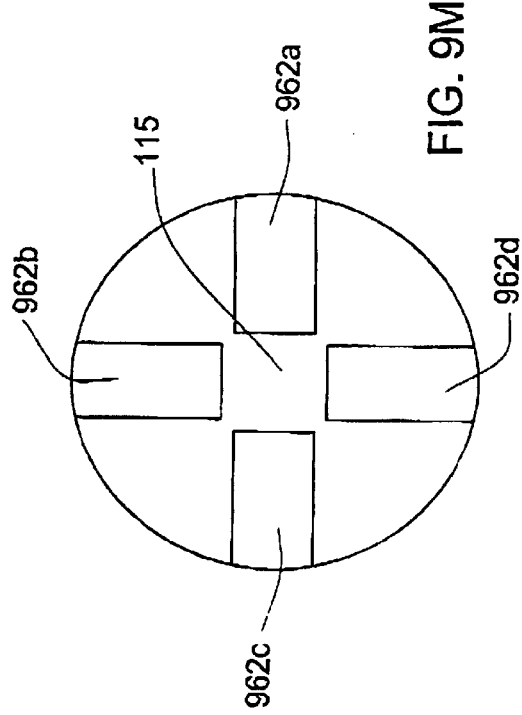

In the embodiment shown in FIG. 9i and 9j the body 95 comprises a rod 950. The rod 950 is hinged at one end to the interior of a hemispherical base 955 by means of a hinge 956. The body 95 is in a sealing orientation when the rod 950 is perpendicular to the base 955 so that a hole 960 located in the base 955 is closed as shown in FIG. 9i. The body 95 is in a non-sealing orientation when rod 950 is rotated about the hinge 956 so that the hole 960 is open as shown in FIG. 9j In yet another embodiment of the body shown in FIG. 9k, and 91 and 9m, a body 96 is formed by introducing four grooves 962a, 962b, 962c and 962d onto the surface of a sphere. The body is shown in three-dimensional perspective in FIG. 9k. In FIG. 91, the body 96 is shown in cross-section through a plane passing through the grooves 962a and 962c. A side view of the body 96 in FIG. 9m shows all four grooves 962a to 962d. Each of the four grooves 962a to 962d extend along about one quarter of a circumference of the sphere and they are all included in a single hemispherical surface 961 of the body 96 located to one side of the circumference indicated by the broken line 963. When the hemispherical to surface 961 containing the grooves 962a to 962d is in contact with the outlet Wall, urine may flow around the body 96 through the grooves 962a to 962d. The body 96 is thus in a non-sealing orientation. When the hemispherical surface 964, located on the opposite side of the circumference 963 is in contact with the outlet wall, the body 96 is in a sealing orientation.

Figure 10:
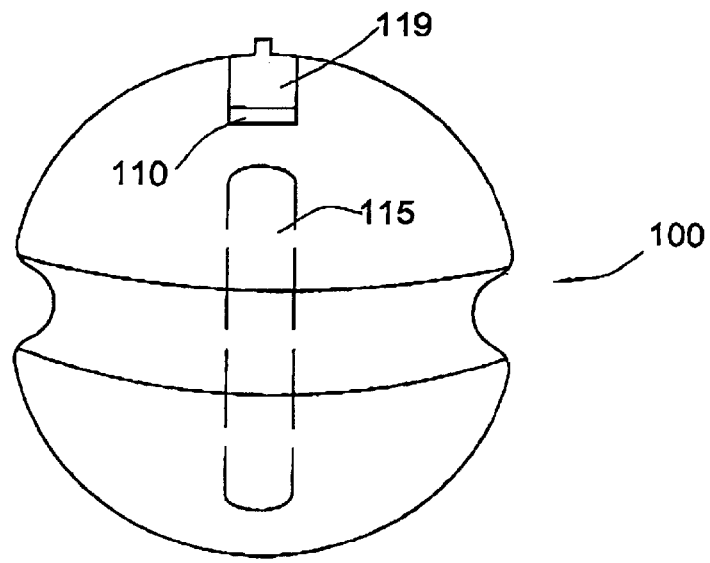
FIG. 10 shows a body comprising an imaging device.
Figure 10:
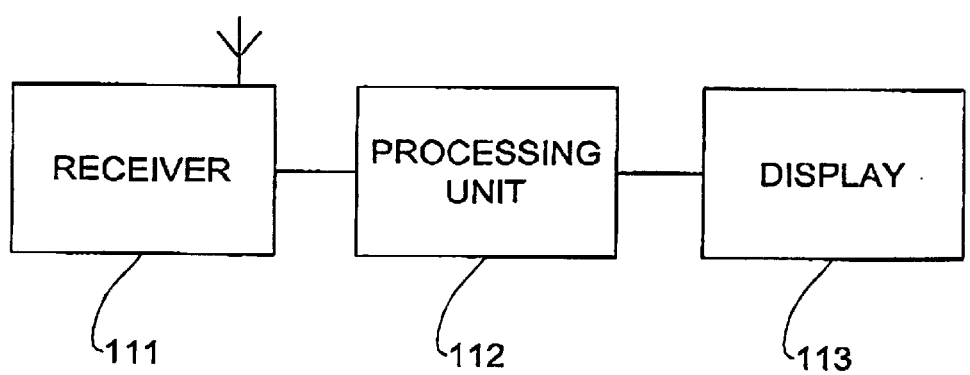

FIG. 10 shows a body 100 constructed so as to comprise an imaging device such as a microvideo camera 119 for imaging the interior of the bladder. The video camera 119 may have associated with it a transmitter 110 for transmitting images to a remote receiver 111. Such microvideo cameras and transmitters are known in the art, for example, as disclosed in U.S. Pat. Nos. 5,604,531, 5,579781 and 5,188,109. The receiver 111 may be connected to a processing unit 112 for processing the images, or a display 113 for displaying images.

Figure 11:
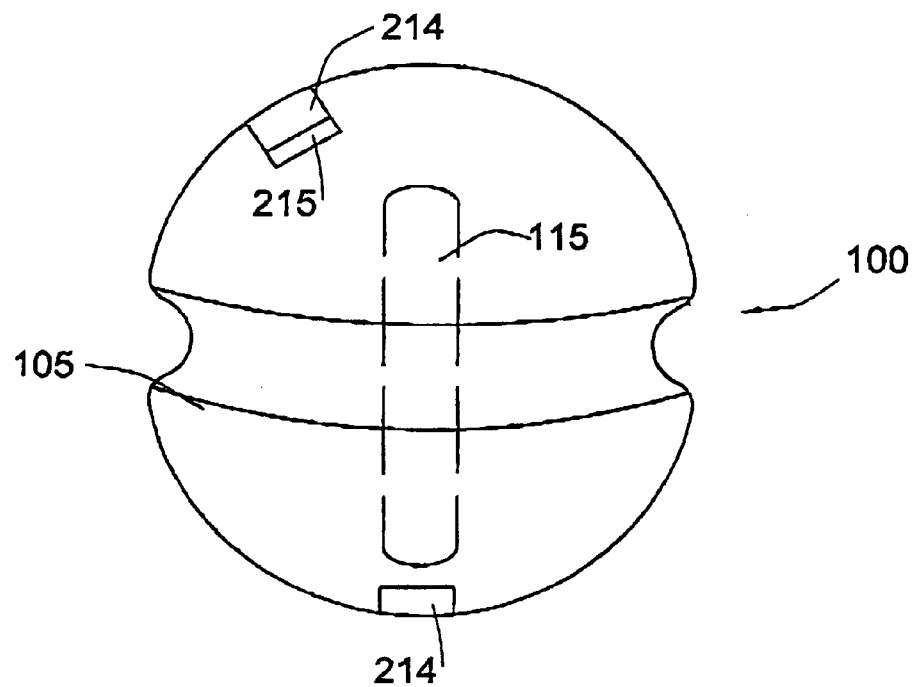
FIG. 11 shows a body comprising devices for measuring urinary bladder parameters.
Figure 11:
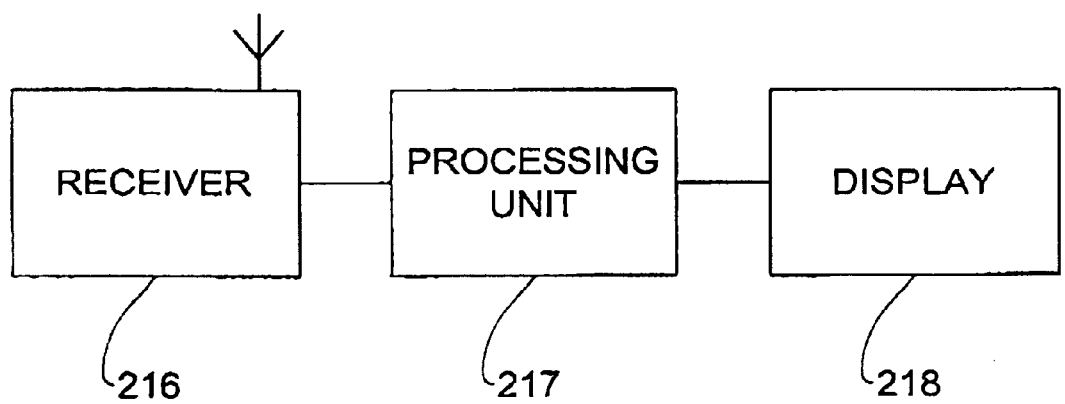

FIG. 11 shows a body 100 constructed so as to comprise one or more devices 214 for measuring one or more parameters associated with the urinary bladder, for example, bladder pressure, bladder volume, urine temperature, urine density, urine conductivity or urine composition. The measuring devices 214 may have associated with it a transmitter 215 for transmitting measurements to a remote receiver 216. The receiver may be connected to a processing unit 217 for processing the measurements or to a display 218 for displaying results. Such measuring devices are known in the art, for example as disclosed in U.S. Pat. Nos. 5,579,781 and 5,188,109.

Figure 12:
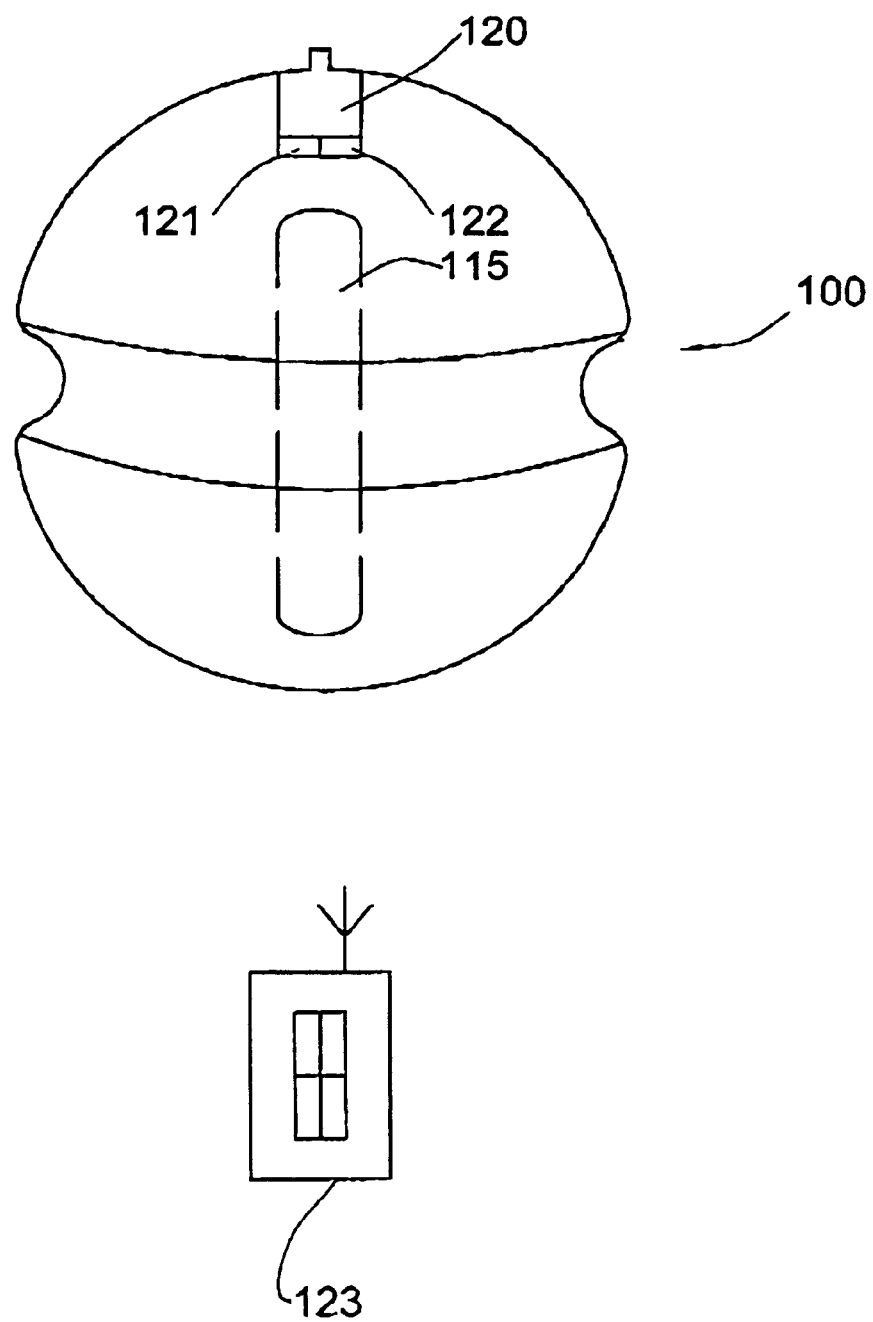
FIG. 12 shows a body comprising a pump.

FIG. 12 shows a body 100 comprising a pump 120 for the controlled release of one or more substances into the bladder. The pump 120 has a reservoir 121 for storing the substances. The pump 120 may have a receiver 122 for receiving signals from a remote control 123. The rate of release of the substance may thus be varied at will using the remote control. Such flow controllers are known in the art, for example, as disclosed in U.S. Pat. Nos. 5,593,134 and 5,996,954.

Figure 19:
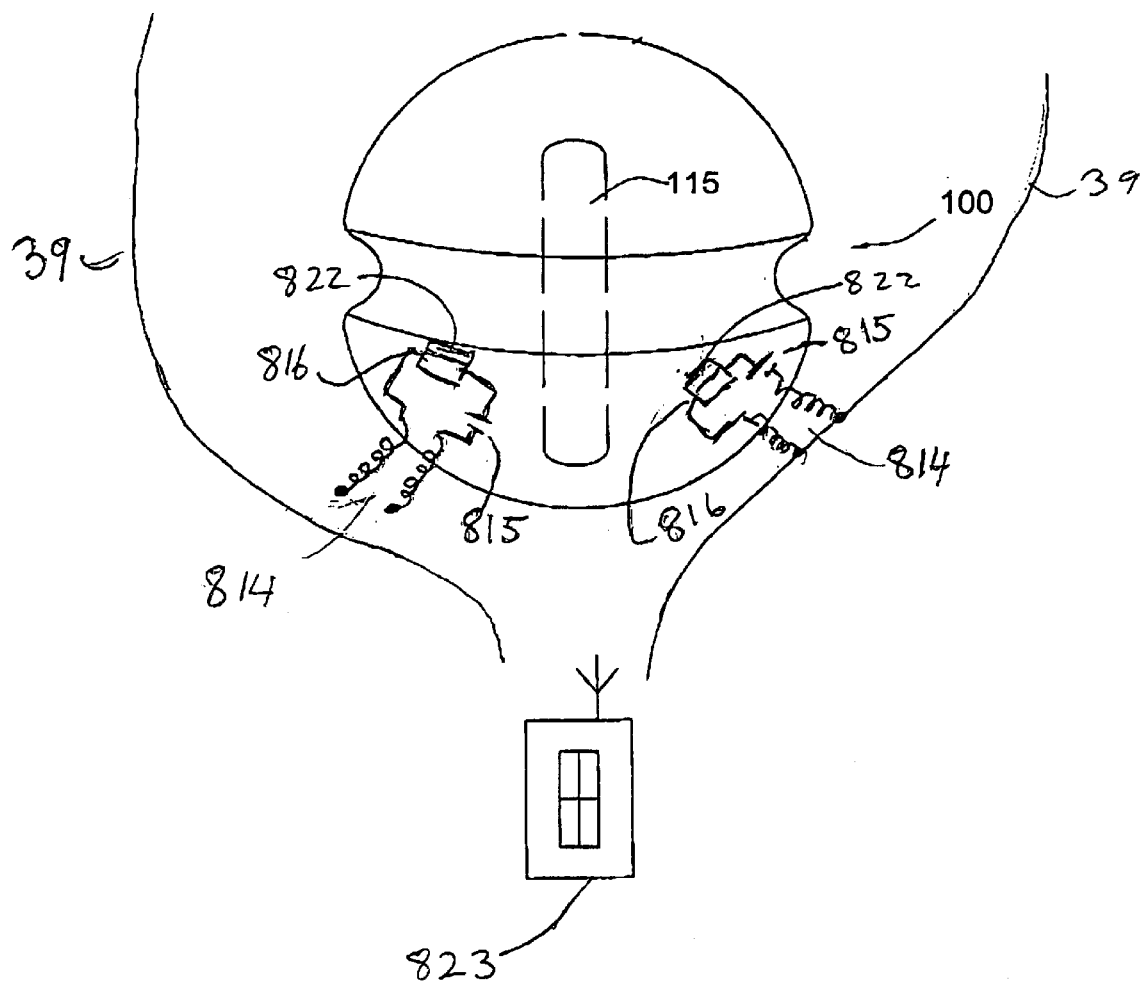
FIG. 19 shows a body comprising one or more electrode pairs.

FIG. 19 shows a body 100 constructed so as to comprise one or more electrode pairs 814 on its surface for use in stimulating a hypotonic urinary bladder. The electrode pairs are part of a circuit that includes a battery 815 and a remote controlled switch 816. A receiver 822 in the switch receives signals from a remote control 823 that is used to open and close the switch 816. When the switch 816 is closed a voltage is applied across the electrode pairs 814. When the electrodes are in contact with the wall of the urinary bladder 39, for example, the region 68 in FIG. 6, and a voltage is applied across the electrode muscle fibers in the bladder wall are stimulated to contract.

The invention has been described with a certain degree of particularly only for the sake of clarity. However, several variations and modifications in the invention are possible without exceeding the scope and spirit of the invention as defined in the following set of claims.

What is claimed is:

1. A resiliently flexible body having a magnetizable portion for use in medical procedures within an outlet of a cavity of an individual, the body having a non-spherical shape and configured to rotate within the outlet between a sealing orientation and a non-sealing orientation.

2. The body according to claim 1, having a spherical surface with one or more grooves therein.

3. The body according to claim 1, having a spherical surface with a circumferential protrusion.

4. The body according to claim 1, having a spherical surface and a channel extending along the length of a diameter of the body.

5. The body according to claim 1, having a tapered shape.

6. The body according to claim 1, comprising a base having a hole, and a plug configured to rotate between an orientation in which the hole is open and an orientation in which the hole is closed.

7. The body according to claim 1 wherein the body is coated on at least a portion of an outer surface with a hydrophilic coating.

8. The body according to claim 1 wherein the body is capable of storing one or more compounds and releasing them into the urinary bladder.

9. The body according to claim 8, wherein at least one substance is selected from the group consisting of antibiotics, anti-microbial agents, drugs, radioactive substances, contrast agents, and substances having a local or systemic effect on cells or tissues of the individual.

10. The body according to claim 1, wherein the cavity is a urinary bladder.

11. The body according to claim 1, having a solid wall and a lumen containing a fluid.

12. The body according to claim 1, having associated with it an imaging device for imaging the cavity.

13. The body according to claim 1, having associated with it a measuring device for measuring a parameter of the cavity.

14. The body according to claim 13, wherein the measuring device measures a parameter selected from tie group consisting;
    (a) a pressure in the cavity;
    (b) a volume of the cavity;
    (c) a temperature of a fluid in the cavity;
    (d) a density of a fluid in the cavity;
    (e) a conductivity of a fluid in the cavity; and
    (f) the composition of a fluid in the cavity.

15. The body according to claim 1, having associated with it a pump for storing and releasing substances into the cavity.

16. The body according to claim 1, having associated with it an electrode pair configured to apply an electrical stimulus to a wall of the cavity.

17. A method of activating a wall of a hypotnic cavity comprising steps of:
    (a) compressing a body according to claim 16;
    (b) inserting the body into the cavity;
    (c) expanding the body in the cavity;
    (d) activating an electrode pair associated with the body using a remote control.

18. A system for use in medical procedures within a cavity of an individual comprising a body according to claim 1, and one or more devices selected from the group consisting:
    (a) an applicator for inserting the body into the cavity or for removing the body from the oavity, the applicator fitted at an end thereof with a gripping device for releasably gripping the body; and
    (b) a rotating member comprising a magnetizable portion for rotating the body in an outlet of the cavity between the sealing orientation and the non-sealing orientation.

19. The system according to claim 18, wherein the cavity is a urinary bladder.

20. The system according to claim 18 wherein the body comprises a device which can emit or absorb a signal detectable by an apparatus for imaging the cavity.

21. The system according to claim 20, wherein said device further comprises a transmitter transmitting signals to a receiver.

22. The system according to claim 21 further comprising a receiver receiving signals from the transmitter.

23. The system according to claim 22 further comprising one or more components selected from the list consisting:
    (a) a processing unit processing signals received by the receiver;
    (b) a display for displaying signals received by the receiver;
    (c) a display for displaying an output produced by the processing unit.

24. The system according to claim 21 for use in imaging the cavity.

25. The system according to claim 18, wherein the body comprises one or more monitoring devices for sampling a morphological or physiological parameter of the cavity and for emitting a signal indicative of a quality or quantity of a sampled parameter.

26. The system according to claim 25, wherein at least one of the devices monitors a parameter of the cavity selected from the group consisting of pressure, temperature, fluid density, fluid conductivity, and fluid composition.

27. The system according to claim 26, wherein the fluid is urine.

28. The system according to claim 26 wherein the immobilizing member is in the form of a hygienic pad adapted to be placed in the individual's underwear.

29. The system according to claim 25, further comprising a transmitter transmitting signals from a monitoring device to a receiver.

30. The system according to claim 29 further comprising a receiver receiving signals from the transmitter.

31. The system according to claim 30, further comprising one or more components selected from the list consisting:
    (a) a processing unit processing signals received by the receiver;
    (b) a display for displaying signals received by the receiver;
    (c) a display for displaying an output produced by the processing unit.

32. The system according to claim 25 for monitoring the cavity.

33. The system according to claim 18 further comprising an immobilizing member comprising a magnetizable portion, the immobilizing member being fitted for securing onto the individual's body for immobilizing the body in the outlet.

34. The system according to claim 18 for use in the treatment of a disorder selected from the group consisting of urinary incontinence, urinary bladder infections, urinary bladder tumors, and bladder dysfunction.

35. The system of claim 18 wherein the gripping device comprises a magnetizable portion for securing the body thereto during application by means of a magnetic interaction.

36. The system according to claim 18, wherein the body has associated with it electrodes configured to apply an electrical stimulus to a wall of the cavity, the system further comprising a remote control for activating the deactivating the electrodes.

37. The system according to claim 36 for use in activating a wall of a hypotonic cavity.

38. The system according to claim 18 for releasing one or more substances in the cavity.

39. A method for treating urinary incontinence in an individual comprising the steps of:
   (a) compressing a body, according to claim 1;
   (b) inserting the body into a urinary bladder outlet of the individual;
   (c) expanding the body in the urinary bladder outlet;
   (d) rotating the body within the urinary bladder outlet into a sealing position for sealing the urinary bladder outlet; and
   (e) rotating the body within the urinary bladder outlet into an unsealing position for voiding the bladder.

40. The method according to claim 39 wherein the body is coated on its outer surface with a hydrophilic coating.

41. A method for releasing one or more substances into the cavity of an individual comprising the steps of:
   (a) loading the one or more substances into a solid, flexibly resilient body according to claim 1;
   (b) compressing the body;
   (c) inserting the body into the cavity; and
   (d) expanding the body in the cavity.

42. The method of claim 41 wherein one or more of the one or more substances are selected from the list consisting of antibiotics, anti-microbial agents, drugs, radioactive substances, contrast agents, and substances having a local or systemic effect on cells or tissues of the individual.

43. The method of claim 41, wherein the cavity is a urinary bladder.

44. A method for monitoring the interior of the cavity of an individual comprising the steps of:
   (a) compressing a body according to claim 1, comprising one or more devices for monitoring the cavity;
   (b) inserting the body into the cavity;
   (c) expanding the body in the cavity; and
   (d) transmitting signals from at least one of the monitoring devices to a receiver.

45. The method of claim 44, further comprising one or more steps selected from the list comprising:
   (a) storing the signals in a computer memory;
   (b) displaying the signals on a display;
   (c) processing the signals in a computer processing unit;
   (d) storing results of the processing in a computer memory; and
   (e) displaying results of the processing on a display.

46. The method of claim 44, wherein the cavity is a urinary bladder.

47. A method for imaging the interior of the cavity of an individual comprising the steps of:
   (a) compressing a body according to claim 1, comprising a device for imaging the cavity;
   (b) inserting the body into the cavity;
   (c) expanding the body in the cavity; and
   (d) transmitting signals from the imaging device to a receiver.

48. The method of claim 47, further comprising one or more steps selected from the list comprising:
   (a) storing the signals in a computer memory;
   (b) displaying the signals on a display;
   (c) processing the signals in a computer processing unit;
   (d) storing results of the processing in a computer memory; and
   (e) displaying results of the processing on a display.

49. The method of claim 47, wherein the cavity is a urinary bladder.

50. A method for releasing one or more substances into the cavity of an individual comprising steps of.
   (a) providing a body according to claim 1, comprising a pump fed by a reservoir;
   (b) loading the reservoir with the one or more substances;
   (c) inserting the body into the cavity; and
   (d) activating the pump so as to release the one or more substances into the cavity.

51. The method according to claim 50, wherein the pump is activated by a remote control.

52. The method of claim 50, wherein the cavity is a urinary bladder.

* * * * *